(12) United States Patent
Fujiwara et al.

(10) Patent No.: US 8,057,404 B2
(45) Date of Patent: Nov. 15, 2011

(54) BLOOD SENSOR, BLOOD TESTING APPARATUS, AND METHOD FOR CONTROLLING BLOOD TESTING APPARATUS

(75) Inventors: Masaki Fujiwara, Ehime (JP);
Noriyoshi Terashima, Ehime (JP);
Shusei Aibara, Ehime (JP)

(73) Assignee: Panasonic Corporation, Osaka (JP)

( * ) Notice: Subject to any disclaimer, the term of this patent is extended or adjusted under 35 U.S.C. 154(b) by 60 days.

(21) Appl. No.: 11/545,468

(22) Filed: Oct. 11, 2006

(65) Prior Publication Data

US 2007/0123803 A1 May 31, 2007

(30) Foreign Application Priority Data

Oct. 12, 2005 (JP) ................................. 2005-297506

(51) Int. Cl.
*A61B 5/00* (2006.01)
(52) U.S. Cl. ........................................ 600/584; 600/181
(58) Field of Classification Search .................. 600/573, 600/584, 576, 579, 583; 204/403.14; 606/181–183
See application file for complete search history.

(56) References Cited

U.S. PATENT DOCUMENTS

| | | | | |
|---|---|---|---|---|
| 5,700,695 A * | 12/1997 | Yassinzadeh et al. | ......... | 436/180 |
| 6,071,251 A * | 6/2000 | Cunningham et al. | ........ | 600/584 |
| 6,159,233 A * | 12/2000 | Matsuzawa | .................... | 606/223 |
| 6,193,873 B1 * | 2/2001 | Ohara et al. | .................. | 205/792 |
| 6,419,661 B1 * | 7/2002 | Kuhr et al. | ..................... | 604/207 |
| 6,506,168 B1 * | 1/2003 | Fathallah et al. | ............. | 600/578 |
| 6,607,658 B1 * | 8/2003 | Heller et al. | ................ | 205/777.5 |
| 6,612,111 B1 * | 9/2003 | Hodges et al. | ................... | 60/583 |
| 6,641,533 B2 * | 11/2003 | Causey et al. | .................. | 600/300 |
| 6,706,159 B2 * | 3/2004 | Moerman et al. | ........ | 204/403.03 |
| 6,790,327 B2 * | 9/2004 | Ikeda et al. | ................. | 204/403.1 |
| 2002/0004196 A1* | 1/2002 | Whitson | ............................ | 435/4 |
| 2002/0022789 A1* | 2/2002 | Perez et al. | ................... | 600/573 |
| 2002/0130042 A1* | 9/2002 | Moerman et al. | ........ | 204/403.01 |
| 2002/0168290 A1* | 11/2002 | Yuzhakov et al. | .............. | 422/56 |
| 2002/0187556 A1* | 12/2002 | Shartle et al. | .................. | 436/149 |
| 2002/0198444 A1* | 12/2002 | Uchigaki et al. | .............. | 600/345 |
| 2003/0018282 A1* | 1/2003 | Effenhauser et al. | ......... | 600/583 |
| 2003/0083685 A1* | 5/2003 | Freeman et al. | .............. | 606/181 |
| 2003/0130597 A1* | 7/2003 | Marshall | ........................ | 600/583 |
| 2003/0144608 A1* | 7/2003 | Kojima et al. | ................. | 600/583 |
| 2003/0223906 A1* | 12/2003 | McAllister et al. | .............. | 422/58 |
| 2004/0186394 A1* | 9/2004 | Roe et al. | ....................... | 600/583 |
| 2004/0186500 A1* | 9/2004 | Koike et al. | .................. | 606/181 |
| 2004/0249310 A1* | 12/2004 | Shartle et al. | .................. | 600/583 |
| 2005/0245844 A1* | 11/2005 | Mace et al. | .................... | 600/583 |
| 2006/0100654 A1* | 5/2006 | Fukuda et al. | ................. | 606/181 |

FOREIGN PATENT DOCUMENTS

| | | | |
|---|---|---|---|
| EP | 1034740 A1 * | 9/2000 | |
| EP | 1 691 192 | 8/2006 | |
| JP | 2002-219114 | 8/2002 | |
| WO | 2005/054840 | 6/2005 | |

* cited by examiner

*Primary Examiner* — Max Hindenburg
*Assistant Examiner* — Michael C Stout
(74) *Attorney, Agent, or Firm* — Wenderoth, Lind & Ponack, LLP

(57) ABSTRACT

A blood sensor including a base (12), a detection part (16) disposed on the base (12), a blood collection needle (13) disposed at a front end (12a) of the base (12), a negative pressure generation part (17) for applying negative pressure to a portion of the blood collection needle (13), and a supply path (15) for supplying blood collected by the blood collection needle (13) to a detection part (16).

22 Claims, 11 Drawing Sheets

BLOOD SENSOR, BLOOD TESTING APPARATUS, AND METHOD FOR CONTROLLING BLOOD TESTING APPARATUS

FIELD OF THE INVENTION

The present invention relates to a blood sensor, a blood testing apparatus, and a method for controlling the blood testing apparatus.

BACKGROUND OF THE INVENTION

Hereinafter, a conventional blood sensor and a blood testing apparatus using the blood sensor will be described with respect to a sensor and a testing apparatus used for diabetes testing.

A diabetic patient measures his/her blood glucose level periodically, and injects insulin on the basis of the blood glucose level to keep a normal blood glucose level. Conventionally, in order to measure blood glucose level, a small amount of blood is collected from a finger tip or the like of a patient using a puncture unit, and then the blood glucose level of the collected blood is measured using a measurement unit.

More specifically, as shown in FIG. 14, initially a puncture needle port 2 of a puncture unit 1 is applied to a finger tip or the like of a patient. Thereafter, a button 3 is pressed. Then, a needle protrudes from the puncture needle port 2 at high speed and goes back instantly, whereby the needle makes a minute wound on the finger tip or the like. The patient squeezes blood from this wound to collect the same.

Next, using a testing unit 4 for measuring blood glucose level shown in FIG. 15, the patient applies the collected blood onto a blood attachment part 5a of a sensor 5 that is inserted in the testing unit 4. Thereby, the testing unit 4 calculates blood glucose level of the attached blood, and displays the result of calculation on a display unit 6.

As prior art document information relating to the invention of this application, for example, Japanese Published Patent Application No. 2002-219114, and a brochure of International Publication No. 2005/054840 are known.

In the conventional testing of blood glucose level, however, it is necessary to use two units, i.e., the puncture unit 1 and the testing unit 4. That is, it is necessary for the patient to make a wound on his/her skin at a finger tip or the like, squeeze blood from this wound, and apply the blood onto the blood attachment part 5a of the sensor 5. This operation is very complicated.

SUMMARY OF THE INVENTION

The present invention is made to solve the above-described problems and has for its objective to provide a blood sensor and a blood testing apparatus with which blood testing can be easily carried out, and a method for controlling the blood testing apparatus.

Other objects and advantages of the invention will become apparent from the detailed description that follows. The detailed description and specific embodiments described are provided only for purposes of illustration since various additions and modifications within the scope of the invention will be apparent to those of ordinary skill in the art from the detailed description.

According to a first aspect of the present invention, a blood sensor comprises a base, a hollow needle for blood collection which is disposed at a front end of the base; a detection part for detecting a component of blood collected by the blood collection needle and a blood supply path for supplying the blood collected by the blood collection needle to the detection part, which are provided in the base, and a negative pressure generation part for applying negative pressure to the hollow part of the blood collection needle through a negative pressure supply path, which is provided in approximately the center of the base.

Therefore, it is possible to provide a blood sensor which can supply the blood collected by the blood collection needle to the detection part without intervening manual work, and detect the blood.

According to a second aspect of the present invention, in the blood sensor according to the first aspect, the blood supply path shares a portion with the negative pressure supply path that forms the negative pressure generation part, and the detection unit is provided at an end of the blood supply path that shares a portion with the negative pressure supply path.

Therefore, it is possible to fabricate a blood sensor in a simple construction.

According to a third aspect of the present invention, in the blood sensor according to the first aspect, detection electrodes are disposed on the detection part, and contact electrodes connected to the detection electrodes are disposed on an end surface of the base.

According to a fourth aspect of the present invention, in the blood sensor according to the first aspect, the blood collection needle comprises plastic.

Therefore, the blood collection needle can be easily fabricated, and needle-stick accidents can be reduced.

According to a fifth aspect of the present invention, in the blood sensor according to the first aspect, the hollow blood collection needle has a circular cross section.

Therefore, the blood collection needle can easily be set on the blood sensor, and thereby fabrication is facilitated.

According to a sixth aspect of the present invention, in the blood sensor according to the first aspect, the hollow blood collection needle has a triangular cross section.

According to a seventh aspect of the present invention, in the blood sensor according to the first aspect, the hollow blood collection needle has a polygonal cross section.

Therefore, the thickness of the tip of the blood collection needle is increased, whereby the strength of the needle tip can be increased.

According to an eighth aspect of the present invention, in the blood sensor according to the first aspect, a blood collection needle cover that covers the blood collection needle is formed integrally with the base.

Therefore, it is possible to provide a safe and preferable blood sensor.

According to a ninth aspect of the present invention, in the blood sensor according to the first aspect, a plurality of the blood collection needles are provided in parallel with each other at the front end of the base.

Therefore, it is possible to provide a highly reliable and safe blood sensor.

According to a tenth aspect of the present invention, in the blood sensor according to the first aspect, at least one surface of the detection part comprises a transparent material.

Therefore, the scale of the blood sensor can be reduced.

According to an eleventh aspect of the present invention, a blood testing apparatus comprises a cylindrical casing, a slider that is forward or backward movably provided in the cylindrical casing, a blood sensor that is attached at a front end of the slider; a first negative pressure generator for supplying negative pressure to a negative pressure generation part provided in the blood sensor, and a blood collection button for instructing the slider to move forward.

Therefore, it is possible to provide a blood sensor which can supply the blood collected by the blood collection needle to the detection part without intervening manual work, and detect the blood.

According to a twelfth aspect of the present invention, in the blood testing apparatus according to the eleventh aspect, a cylindrical cap is provided at a front end of the casing.

Therefore, the blood collection needle is not exposed, whereby safety is secured, and the patient is not scared by the needle. Furthermore, even when the blood testing apparatus is dropped to the floor, accidents such as breakage of the blood collection needle are avoided.

According to a thirteenth aspect of the present invention, the blood testing apparatus according to the eleventh aspect further includes a second negative pressure generator for supplying negative pressure, which is provided in the casing.

Therefore, a measurement site of a patient can be easily punctured with the blood collection needle.

According to a fourteenth aspect of the present invention, in the blood testing apparatus according to the eleventh aspect, forward movement of the slider is given momentum by a coil spring.

Therefore, puncture to a measurement site of a patient can be carried out more easily.

According to a fifteenth aspect of the present invention, the blood testing apparatus according to the eleventh aspect further includes a vibration generator for vibrating the blood collection needle.

Therefore, blood collection can be carried out more easily.

According to a sixteenth aspect of the present invention, a blood testing apparatus comprises a cylindrical casing, a slider that is forward or backward movably provided in the cylindrical casing, a blood sensor that is attached at a front end of the slider, a first negative pressure generator for supplying negative pressure to a negative pressure generation part provided in the blood sensor, a blood collection button for instructing the slider to move forward, contact terminals to which the contact electrodes provided in the blood sensor are connected, the contact terminals being provided on the slider, and a measurement unit for measuring a component of blood that is collected and detected by the blood sensor, the measurement unit being connected to the contact terminals.

Therefore, the blood collected by the blood collection needle can be supplied to the detection part without intervening manual work to measure components of the blood.

According to a seventeenth aspect of the present invention, in the blood testing apparatus according to the sixteenth aspect, the measurement unit comprises an I/V converter connected to the contact terminals, an A/D converter to which an output of the I/V converter is connected, an operation unit having an input to which an output of the A/D converter is connected, and the other input to which an output of a control unit is connected, and a display unit to which an output of the operation unit is connected.

Therefore, the components of the collected blood can be measured and displayed.

According to an eighteenth aspect of the present invention, the blood testing apparatus according to the seventeenth aspect further includes a transmission unit for transmitting the result of operation obtained by the operation unit, the transmission unit being connected to the control unit.

Therefore, the result of operation obtained by the blood testing apparatus can be transmitted to another apparatus to set a value based on the result of operation of the apparatus, and thereby a setting error on the apparatus can be avoided.

According to a nineteenth aspect of the present invention, a method for controlling a blood testing apparatus comprises an attachment step of attaching the blood sensor to the blood testing apparatus, a puncture preparation step of applying the blood testing apparatus to a measurement site, after the attachment step, a puncture operation step of puncturing the measurement site with the blood collection needle, after the puncture preparation step, a blood collection step of applying negative pressure to the hollow part of the blood collection needle by the first negative pressure generator to collect blood from the measurement site, after the puncture operation step, and a measurement step of detecting and measuring a component of the collected blood, after the blood collection step.

Therefore, the blood collected by the blood collection needle can be supplied to the detection part without intervening manual work to measure components of the blood.

According to a twentieth aspect of the present invention, in the method for controlling a blood testing apparatus according to the nineteenth aspect the blood collection needle is vibrated by the vibration generator in the blood collection step.

Therefore, blood collection can be facilitated.

According to a twenty-first aspect of the present invention, in the method for controlling a blood testing apparatus according to the nineteenth aspect, in the attachment step, a cap is put on the front end of the casing of the blood testing apparatus after a blood collection needle cover that covers the blood collection needle of the blood sensor is removed.

Therefore, the blood collection needle is prevented from scaring the patient, and accidents such as breakage of the needle can be avoided.

According to a twenty-second aspect of the present invention, in the method for controlling a blood testing apparatus according to the twenty-first aspect, in the puncture preparation step, the cap is applied to a measurement site, and negative pressure is added into the casing the blood testing apparatus including the cap by the second negative pressure generator.

Therefore, the measurement site of the patient can be easily punctured with the blood collection needle.

According to twenty-third aspect of the present invention, in the method for controlling a blood testing apparatus according to the nineteenth aspect, after the measurement step, the measured data are transmitted to an injection unit for a curative drug.

Therefore, a dose of insulin to be administered to the patient can be automatically set on the injection unit, whereby the patient is saved from the trouble of setting the dose of insulin on the injection unit. Further, the dose of insulin can be set on the injection unit without intervening manual work, thereby avoiding setting error.

EFFECTS OF THE INVENTION

The blood sensor according to the present invention is provided with the base; the detection part disposed in the base, the hollow blood collection needle provided at the front end of the base, the negative pressure generation part for applying negative pressure to the blood collection needle, and the supply path for supplying the blood collected by the blood collection needle to the detection part. Since the blood sensor itself has the blood collection needle, the skin of the patient can be punctured with the blood collection needle, and simultaneously, blood can be collected with the needle.

Moreover, the collected blood is guided as it is to the detection part without intervening manual work to be tested as it is.

Accordingly, in the blood testing apparatus provided with the above-mentioned blood sensor and the method for controlling the blood testing apparatus, there is no burden of using a puncture apparatus and a measurement apparatus separately, and blood collection and testing can be easily carried out.

BRIEF DESCRIPTION OF THE DRAWINGS

FIG. 3(a) is a plan view of a cover of the blood sensor, FIG. 3(b) is a plan view of a spacer of the blood sensor, FIG. 3(c) is a plan view of a substrate of the blood sensor, and FIG. 3(d) is a plan view of an assembled blood sensor.

FIG. 4(a) is front and side views of a needle having a triangle side surface, FIG. 4(b) is front and side views of a needle having a circular side surface, FIG. 4(c) is front and side views of a needle having a rectangle side surface, and FIG. 4(d) is front and side views of a needle having a hexagonal side surface.

FIG. 5(a) is a plan view before disconnection of the needle cover for a cover, FIG. 5(b) is a plan view before disconnection of the needle cover for a spacer, FIG. 5(c) is a plan view before disconnection of the needle cover for a substrate, and FIG. 5(d) is a plan view of an assembled blood sensor.

FIG. 10(a) is a cross-sectional view of the apparatus showing attachment of a blood sensor, FIG. 10(b) and FIG. 10(c) are cross-sectional views of the apparatus during puncture preparation, FIG. 10(d) is a cross-sectional view of the apparatus during puncture operation, and FIG. 10(e) is a cross-sectional view of the apparatus during blood collecting operation.

DETAILED DESCRIPTION OF THE PREFERRED EMBODIMENTS

Hereinafter, embodiments of the present invention will be described with reference to the drawings.

Embodiment 1

Figure 1:
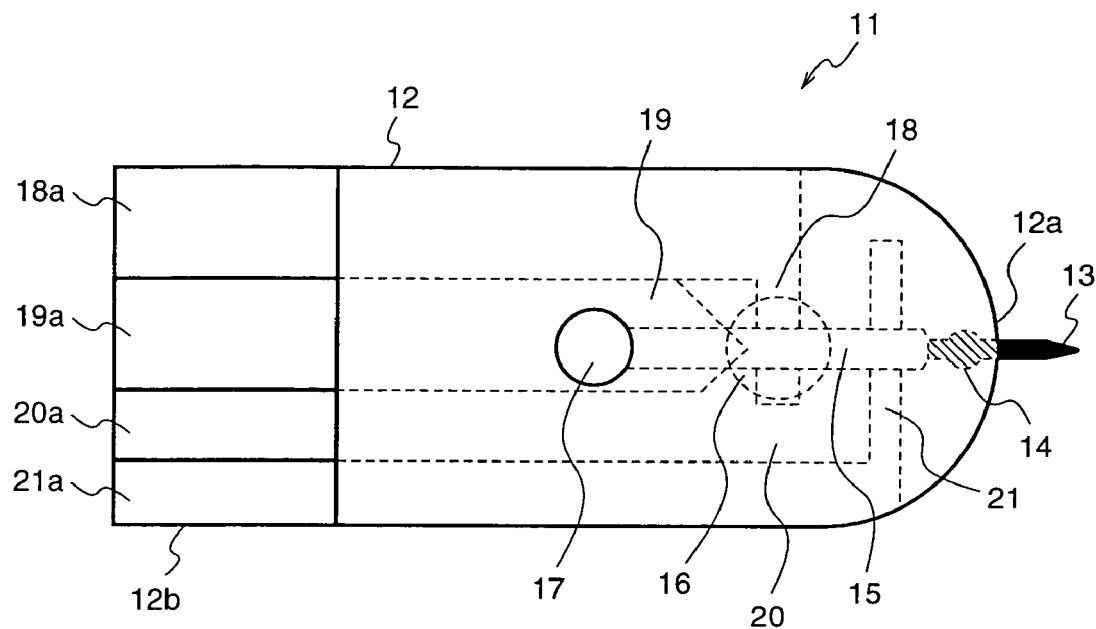
FIG. 1 is a plan view of a blood sensor according to a first embodiment of the present invention.

FIG. 1 is a plan view illustrating a blood sensor 11 according to a first embodiment of the present invention.

With reference to FIG. 1, a base 12 of the blood sensor 11 has a bell shape, and a hollow needle for blood collection is attached to a front end 12a of the base 12. A blood supply path 16a for supplying the blood component collected by the blood collection needle 13 to a detection part 16 is led from a attachment part 14 to which the blood collection needle 13 is attached, and this blood supply path 16a shares a portion with a negative pressure supply path 17c that forms a negative pressure generation part 17 for applying negative pressure to the follow portion of the blood collection needle 13. In order to simplify the following description, it is assumed that the negative pressure supply path 17c and the blood supply path 16a constitute a supply path 15.

The detection part 16 includes detection electrodes 18, 19, 20, and 21 comprising a conductive material. The detection electrodes 18, 19, 20, and 21 are led to the other end 12b of the base 12, thereby forming contact electrodes 18a, 19a, 20a, and 21a, respectively.

Figure 2:
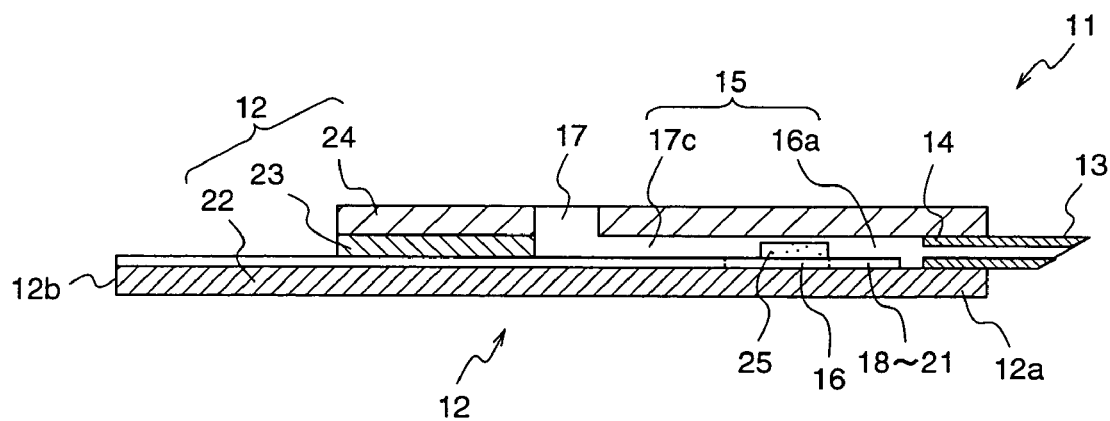
FIG. 2 is a cross-sectional view of the blood sensor according to the first embodiment.

FIG. 2 is a cross-sectional view of the blood sensor 11 according to the first embodiment. With reference to FIG. 2, the base 12 comprises a substrate 22, a spacer 23 that is put on the upper surface of the substrate 22, and a cover 24 that is put on the upper surface of the spacer 23. The blood collection needle 13 is attached to the front end 12a of the base 12, and the supply path 15 extends toward the other end 12b of the base 12 from the attachment part 14 to which the blood collection needle 13 is attached. The detection part 16 is disposed in the middle of the supply path 15, and a reagent 25 is disposed on the detection part 16.

Further, at an end of the supply path 15, the negative pressure generation part 17 is disposed toward the surface side of the cover 24, and negative pressure is supplied from the negative pressure generation part 17 to the blood collection needle 13.

Figure 3A:
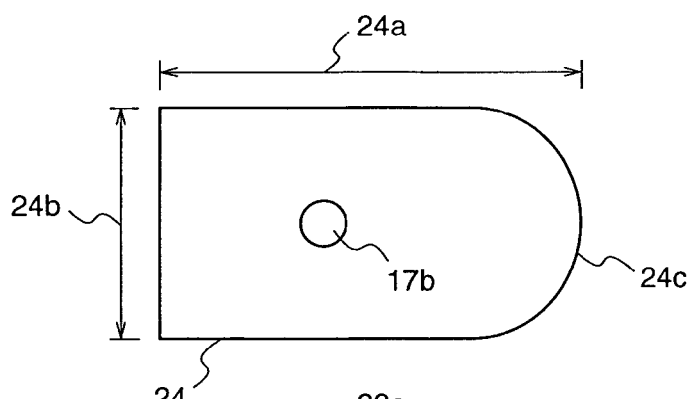
FIGS. 3(a)-3(d) are exploded plan views of the blood sensor according to the first embodiment.
Figure 3B:
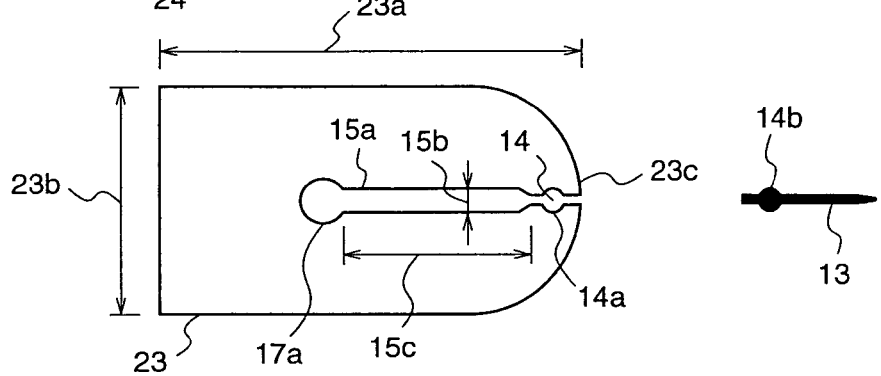
Figure 3C:
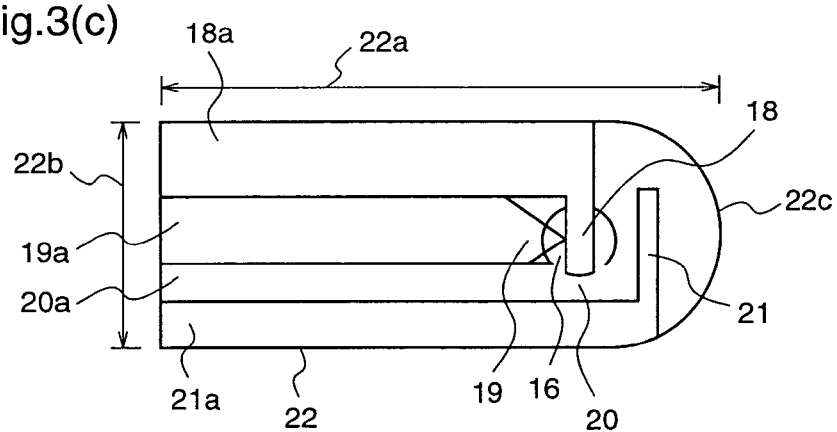

FIGS. 3(a)-3(d) are exploded plan views of the blood sensor 11 according to the first embodiment. FIG. 3(c) is a plan view of the substrate 22, and its width 22a and length 22b are 12 mm and 5 mm, respectively.

Further, a front end 22c of the substrate 22 is semicircular in shape, and a radius of the semicircle is 2.5 mm. The substrate 22 comprises polyethylene terephthalate (PET) having a thickness of 0.5 mm (ranging from 0.1 to 0.6 mm).

A conductive layer is formed on the upper surface of the substrate 22 by depositing gold, platinum, or palladium by sputtering or vapor deposition, and the conductive layer is subjected to laser processing to integrally fabricate the detection electrodes 18~21 and the contact electrodes 18a~21a which are connected to the detection electrodes 18~21, respectively.

FIG. 3(b) is a plan view of the spacer 23 included in the blood sensor 11 according to the first embodiment, and its width 23a and length 23b are 9 mm and 5 mm, respectively. A front end 23c of the spacer 23 is semicircular in shape, and a radius of the semicircle is 2.5 mm. The spacer 23 comprises polyethylene terephthalate (PET) having a thickness of 0.1 mm (ranging from 0.05 to 0.25 mm).

A slit 15a is formed from the front end 23c so as to be connected to a hole 17a that forms the negative pressure generation part 17, and a width 15b and a length 15c of the slit 15a are 0.5 mm and 4.35 mm, respectively. Accordingly, this slit 15a, the substrate 22, and the cover 24 form the supply path 15 having a thickness of 0.1 mm, a width of 0.5 mm, and a length of 4.35 mm. Therefore, when a fluid such as blood is applied to the supply path 15, capillary phenomenon occurs.

Further, an attachment concave part 14a that forms the attachment part 14 is disposed between the front end 23c and a beginning end of the slit 15a, while an attachment convex part 14b that fits the attachment concave part 14a is formed in the blood collection needle 13. Accordingly, the blood collection needle 13 is firmly fixed to the attachment part 14 of the spacer 23.

FIG. 3(a) is a plan view of the cover 24 included in the blood sensor 11 according to the first embodiment. The cover 24 has a width 24a of 9 mm, and a length 24b of 5 mm. A front end 24c of the cover 24 is semicircular in shape, and a radius of the semicircle is 2.5 mm.

Further, a hole 17b having a diameter of 1 mm is formed in the cover 24, and this hole 17b is communicated with the hole 17a formed in the spacer 23, thereby forming the negative pressure generation part 17.

The cover 24 comprises polyethylene terephthalate (PET) having a thickness of 0.1 mm (ranging from 0.05 mm~0.2 mm). A portion of the cover 24 corresponding to a ceiling of the supply path 15 is subjected to hydrophilic processing to make blood flow into the supply path 15 smoothly by capillary phenomenon.

Figure 3D:
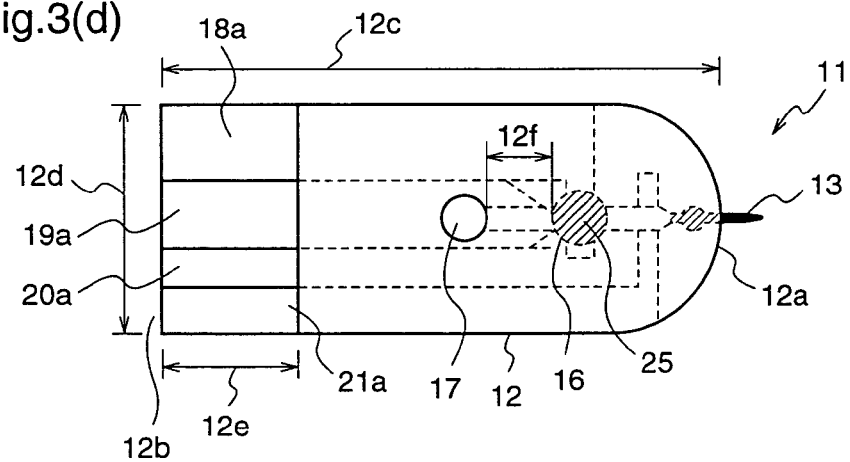

FIG. 3(d) is a plan view of the base 12 of the blood sensor, and a width 12c and a length 12d of the base 12 are 12 mm and 5 mm, respectively. A front end 12a of the base 12 is semicircular in shape, and a radius of the semicircle is 2.5 mm.

The contact electrodes 18a~21a are exposed in a region of the base 12 corresponding to a length 12e from the other end 12b of the base 12.

Further, the spacer 23 and the cover 24 are disposed back by the length 12e from the other end 12b.

A spacing 12f between the detection part 16 and the negative pressure generation part 17 is about 1 mm. This spacing prevents blood from leaking out of the negative pressure generation part 17 when the negative pressure is stopped.

The base 12 is obtained by laminating and adhering the substrate 22, the spacer 23, and the cover 24. Since polyethylene terephthalate (PET) is used as a material of these components, it is easy to manage the base 12.

Further, a reagent 25 is disposed on the detection part 16. The reagent 25 is produced by preparing a reagent solution by adding such as PQQ-GDH and potassium ferricyanide into CMC aqueous solution, dropping the reagent solution onto the detection electrodes 18 and 20 of the substrate 22, and drying the reagent solution.

According to the first embodiment of the present invention, since the blood sensor 11 itself has the blood collection needle 13, it is possible to simultaneously perform puncture of needle into the skin as well as blood collection, using the blood collection needle 13.

Moreover, since the collected blood is guided to the detection part 16 without intervening manual work, the blood can be tested as it is.

Accordingly, blood testing can be easily carried out without the troubles in the conventional apparatus.

Further, since the blood collection needle 13 has the negative pressure generation part 17 for applying negative pressure to the needle, blood collection can be carried out speedily and reliably.

Embodiment 2

FIGS. 4(a)-4(d) are front views and side views of various shapes of blood collection needles 13 according to a second embodiment of the present invention. The same components are given the same reference numerals to simplify the description.

As a material of the blood collection needle 13 shown in FIGS. 4(a)-4(d), metal (SUS304) or plastic (PEEK: polyether ether ketone) may be used. When metal is adopted, a strong and easy-to-puncture blood collection needle 13 can be produced.

When plastic is used, the blood collection needle 13 can be easily fabricated by extrusion molding, and further, the needle 13 has elasticity that reduces needle-stick accidents to the patient.

Figure 4A:
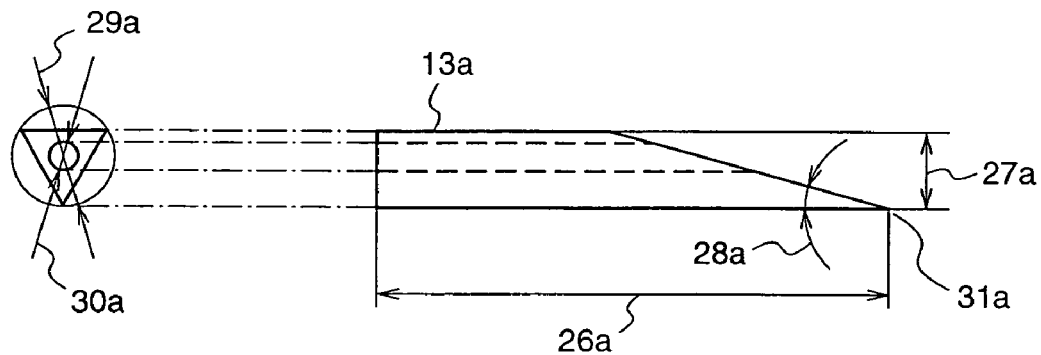
FIGS. 4(a)-4(d) are front views and side views of a blood collection needle according to a second embodiment, of the blood sensor according to the first embodiment.

In FIG. 4(a), a blood collection needle 13a has a triangular side surface, and its length 26a and height 27a are 1 mm and 0.155 mm, respectively. An angle 28a at the front end is 15°. A diameter 29a of the side surface is 0.2 mm, and a through-hole having a diameter 30a of 0.05 mm is formed in the center of the diameter 29a, and the collected blood flows into the through-hole.

As shown in FIG. 4(a), since the blood collection needle 13a of the blood sensor 11 according to the second embodiment has the triangular side surface, the thickness of the front end portion 31a increases, whereby the strength of the needle tip of the blood collection needle 13a can be increased.

Further, since the apex of the triangular shape corresponds to the front end portion 31a, the needle tip becomes sharper, and thereby the needle can easily run into the skin. Further, incorporation of the blood collection needle 13a into the spacer 23 constituting the sensor 11 is also facilitated.

Figure 4B:
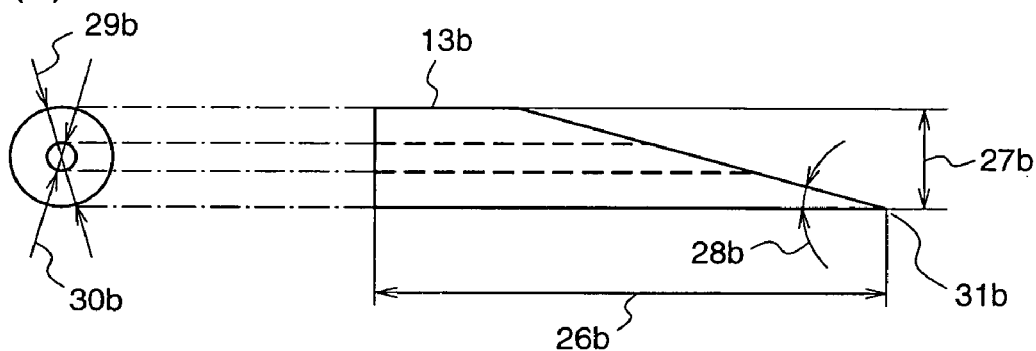

With reference to FIG. 4(b), a blood collection needle 13b has a circular side surface, and its length 26b and height 27b are 1 mm and 0.2 mm, respectively. An angle 28b of a front end portion 31b is 15°. A diameter 29b of the side surface is 0.2 mm. A through-hole having a diameter 30b of 0.05 mm is formed in the center of the diameter 29b, and the collected blood flows into the through-hole.

As shown in FIG. 4(b), since the blood collection needle 13b of the blood sensor 11 according to the second embodiment has the circular side surface, it is possible to incorporate the blood collection needle 13b into the spacer 23 constituting the blood sensor 11, without the necessity of paying attention to the rotation direction, and further, fabrication of the needle 13b is facilitated.

Figure 4C:
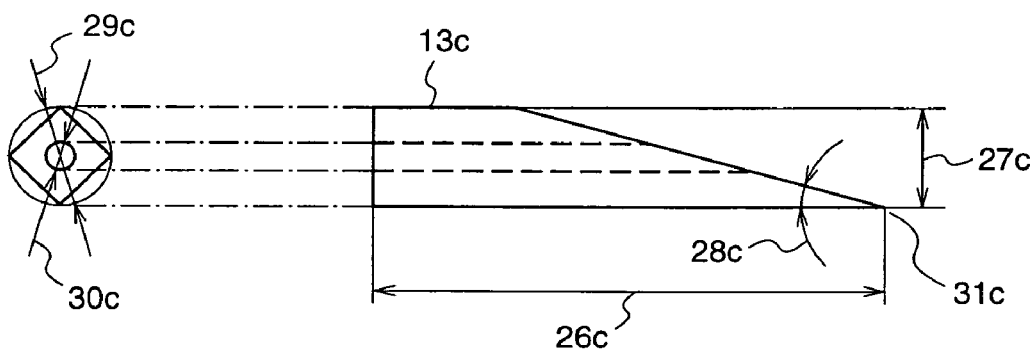

With reference to FIG. 4(c), a blood collection needle 13c has a rectangle side surface, and its length 26c and height 27c are 1 mm and 0.2 mm, respectively. An angle 28c of a front end portion 31c is 15°. A diameter 29c of the side surface is 0.2 mm. A through-hole having a diameter 30c of 0.05 mm is formed in the center of the diameter 29c, and the collected blood flows into the through-hole.

As shown in FIG. 4(c), since the blood collection needle 13c of the blood sensor 11 according to the second embodiment has the rectangular side surface, the thickness of the front end portion 31c increases, whereby the strength of the tip of the blood collection needle 13c can be increased.

Further, since the apex of the rectangular shape corresponds to the front end portion 31c, the needle tip becomes sharper, and thereby the needle can easily run into the skin. Further, incorporation of the blood collection needle 13c into the spacer 23 constituting the sensor 11 is also facilitated.

Figure 4D:
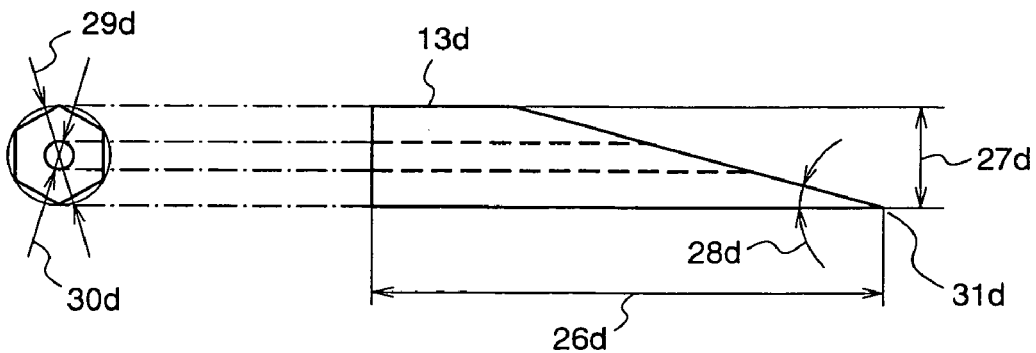

With reference to FIG. 4(d), a blood collection needle 13d has a hexagonal side surface, and its length 26d and height 27d are 1 mm and 0.2 mm, respectively. An angle 28d of a front end portion 31d is 15°. A diameter 29d of the side surface is 0.2 mm. A through-hole having a diameter 30d of 0.05 mm is formed in the center of the diameter 29d, and the collected blood flows into the through-hole.

As shown in FIG. 4(d), since the blood collection needle 13d of the blood sensor 11 according to the second embodiment has the hexagonal side surface, incorporation of the blood collection needle 13d into the spacer 23 constituting the sensor 11 is facilitated.

According to the blood sensor 11 of the second embodiment, metal (SUS304) or plastic (PEEK: polyether ether ketone) is used as a material of the blood collection needle 13. Therefore, when metal is used, a strong and easy-to-puncture blood collection needle 13 can be obtained. On the other hand, when plastic is used, an elastic blood collection needle 13 can be obtained as well as the needle 13 can be easily fabricated by extrusion molding, whereby needle-stick accidents to the patient can be reduced.

Further, when the side surface of the blood collection needle is triangular in shape, the thickness of the front end portion 31a is increased, whereby the strength of the tip of the blood collection needle 13a can be increased. Further, since an apex of the triangular shape of the side surface corresponds to the front end portion 31a, the needle tip becomes sharper and easy to run into the skin, and moreover, incorporation of the needle 13a into the spacer 23 constituting the sensor 11 can be facilitated.

When the side surface of the blood collection needle is circular in shape, it becomes unnecessary to pay attention to the rotation direction when the blood collection needle is incorporated in the spacer 23 constituting the blood sensor 11, and further, fabrication is facilitated.

When the side surface of the blood collection needle is rectangular in shape, the thickness of the front end portion 31c is increased, whereby the strength of the tip of the blood collection needle 13c is increased. Further, since an apex of the rectangular shape of the side surface corresponds to the front end portion 31c, the needle tip becomes sharper and easy to run into the skin, and moreover, incorporation of the blood collection needle into the spacer 23 constituting the blood sensor 11 is facilitated.

When the side surface of the blood collection needle is hexagonal in shape, incorporation of the blood collection needle 13d into the spacer 23 constituting the blood sensor 11 is facilitated.

Embodiment 3

FIGS. 5(a)-5(d) are plan views of a substrate 22, a spacer 23, and a cover 24 which constitute a blood sensor 11 according to a third embodiment of the present invention, before disconnection of a blood collection needle cover. The same components are given the same reference numerals to simplify the description.

Figure 5A:
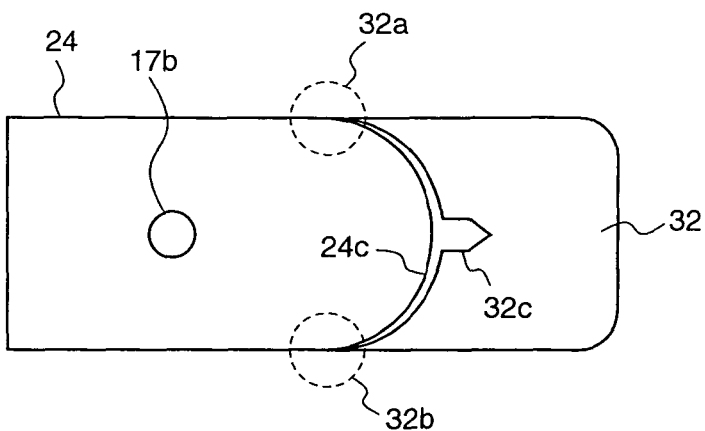
FIGS. 5(a)-5(d) are plan views before disconnection of blood collection needle covers according to a third embodiment of the present invention.

FIG. 5(a) is a plan view of a cover 24 and a blood collection needle cover 32 connected to the cover 24, before disconnection of the needle cover 32, in the blood sensor 11 according to the third embodiment. The blood collection needle cover 32 is formed of the same material as and integrally with the cover 24.

To be specific, the blood collection needle cover 32 is formed so as to cover a front end portion 24c of the cover 24, and is connected to the cover 24 at both ends 32a and 32b of the circular front end portion 24c of the cover 24.

Further, a notch 32c is formed at a position in the blood collection needle cover 32 corresponding to the blood collection needle 13 so that the needle 13 is inserted into the notch 32c with clearance. The notch 32c is a part of the blood collection needle cover 32 that protects the blood collection needle 13.

Figure 5B:
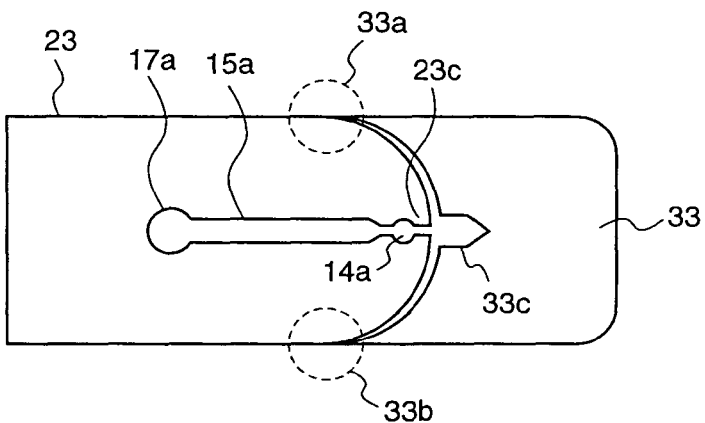

FIG. 5(b) is a plan view of a spacer 23 and a blood collection needle cover 33 connected to the spacer 23, before disconnection of the needle cover 33. The blood collection needle cover 33 is formed of the same material as and integrally with the spacer 23.

To be specific, the blood collection needle cover 33 is formed so as to cover a front end portion 23c of the spacer 23, and is connected to the spacer 23 at both ends 33a and 33b of the circular front end portion 23c of the spacer 23.

Further, a notch 33c is formed at a position in the blood collection needle cover 33 corresponding to the blood collection needle 13 so that the needle 13 is inserted into the notch 33c with clearance. The notch 33c is a part of the blood collection needle cover 33 that protects the blood collection needle 13.

Figure 5C:
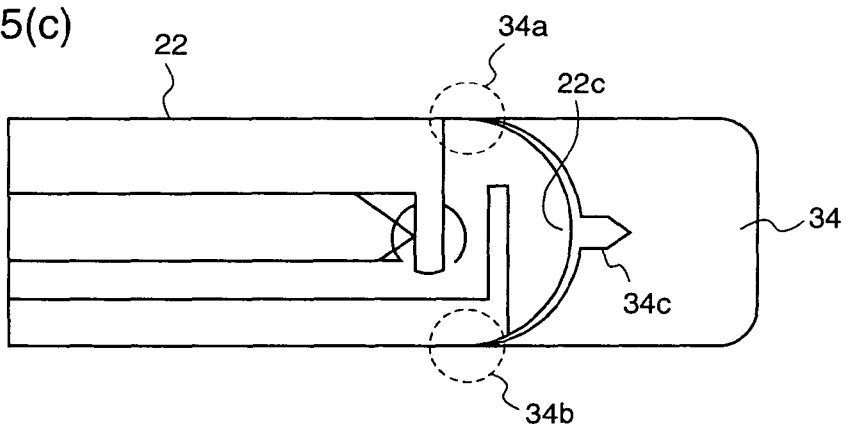

FIG. 5(c) is a plan view of a substrate 22 and a blood collection needle cover 34 connected to the substrate 22, before disconnection of the needle cover 34, in the blood sensor 11 according to the third embodiment. The blood collection needle cover 34 is formed of the same material as and integrally with the substrate 22.

To be specific, the blood collection needle cover 34 is formed so as to cover a front end portion 22c of the substrate 22, and is connected to the substrate 22 at both ends 34a and 34b of the circular front end portion 22c of the substrate 22.

Further, a notch 34c is formed at a position in the blood collection needle cover 34 corresponding to the blood collection needle 13 so that the needle 13 is inserted into the notch 34c with clearance. The notch 34c is a part of the blood collection needle cover 34 that protects the blood collection needle 13.

Figure 5D:
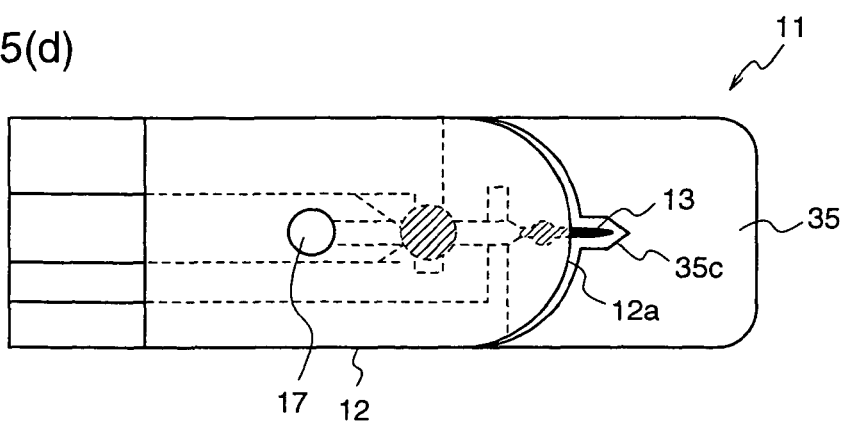

The substrate 22 before disconnection of the blood collection needle cover 34, the spacer 23 before disconnection of the blood collection needle cover 33, and the cover 24 before disconnection of the blood collection needle cover 32 are laminated and adhered to each other, resulting in a blood sensor 11 having a blood collection needle cover 35 with a notch 35c as shown in FIG. 5(d).

The blood collection needle cover 35 is disconnected just before use of the blood sensor 11 to expose the blood collection needle 13.

Accordingly, the patient is not punctured with the blood collection needle 13 before use of the blood sensor 11, and whereby safety is secured.

According to the blood sensor 11 of the third embodiment, the blood collection needle cover 32 is formed of the same material as and integrally with the cover 24 as shown in FIG. 5(a), the blood collection cover 33 is formed of the same material as and integrally with the spacer 23 as shown in FIG. 5(b), and further, the blood collection needle cover 34 is formed of the same material as and integrally with the substrate 22 as shown in FIG. 5(c), and a notch is formed in a portion of each blood collection needle cover 13 corresponding to the blood collection needle 13 so that the blood collection needle 13 is inserted into the notch with clearance, which notch is a part of a blood collection needle cover unit that protects the blood collection needle 13. Since the blood collection needle cover unit is disconnected just before use of the blood sensor 11 to expose the blood collection needle 13, the patient is not punctured with the needle 13 before use of the blood sensor 11, resulting in a safe and favorable blood sensor.

Embodiment 4

Figure 6:
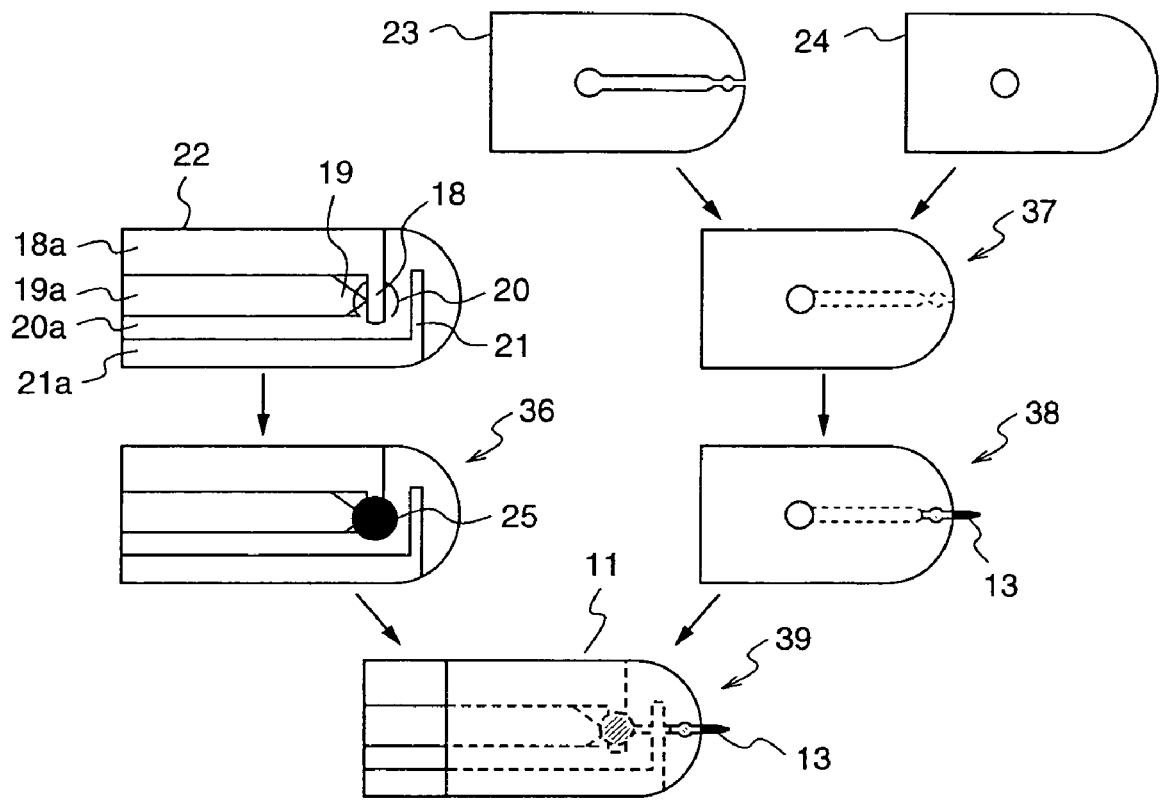
FIG. 6 is a fabrication process chart of a blood sensor according to a fourth embodiment of the present invention.

FIG. 6 is a diagram illustrating a production process of a blood sensor 11 according to a fourth embodiment of the present invention. The same components are given the same reference numerals to simplify the description.

In FIG. 6, reference numeral 36 denotes a reagent application step of applying a reagent 25 on the substrate 22 where the detection electrodes 18~21 are disposed.

Reference numeral 37 denotes a bonding step of bonding the spacer 23 and the cover 24 to each other.

Reference numeral 38 denotes a blood collection needle attachment step of attaching the blood collection needle after the bonding step 37.

Finally, reference numeral 39 denotes a completion step of bonding the substrate 22 on which the reagent 25 is applied in the reagent application step 36 to the spacer 23 and the cover 24 to which the blood collection needle 13 is attached in the blood collection needle attachment step 38.

In these steps, the operations are carried out in the state where the blood collection needle covers 32, 33, and 34 described in the third embodiment are connected.

As described above, the blood sensor fabrication method according to the fourth embodiment comprises the reagent application step 36 of applying the reagent 25 on the substrate 22 where the detection electrodes 18~21 are disposed, the bonding step 37 of bonding the spacer 23 and the cover 24 to each other; the blood collection needle attachment step 38 of attaching the blood collection needle after the bonding step 37, and the completion step 39 of bonding the substrate 22 on which the reagent 25 is applied in the reagent application step 36 to the spacer 23 and the cover 24 to which the blood collection needle 13 is attached in the blood collection needle attachment step 38. Therefore, it is possible to easily fabricate the blood sensor 11.

Embodiment 5

Figure 7:
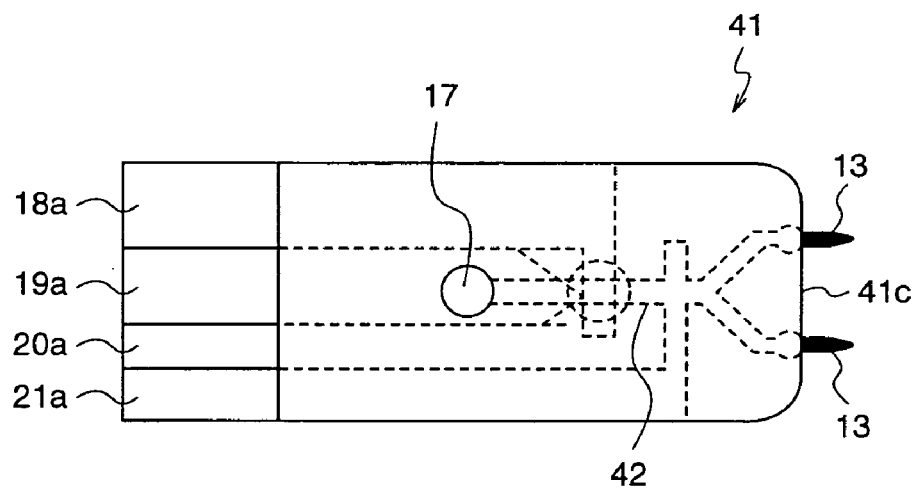
FIG. 7 is a plan view of a blood sensor according to a fifth embodiment of the present invention.

FIG. 7 is a plan view of a blood sensor 41 according to a fifth embodiment of the present invention. In FIG. 7, the same reference numerals as those shown in FIGS. 1 to 6 denote the same components, and therefore, repeated description is not necessary.

The blood sensor 41 according to the fifth embodiment is different from the blood sensor 11 according to the first embodiment in that two blood collection needles 13 are attached to a front end portion 41c of the blood sensor 41 side by side and in parallel with each other.

A supply path 42 is connected to the two blood collection needles 13, respectively.

According to the blood sensor 41 of the fifth embodiment, since the two blood collection needles 13 are disposed side by side and in parallel with each other, the time for blood collection can be reduced.

Further, even when there occurs insufficient aspiration of blood or clogging of one needle, the blood can be supplied from the other needle, resulting in a safe and highly-reliable blood sensor.

Embodiment 6

Figure 8:
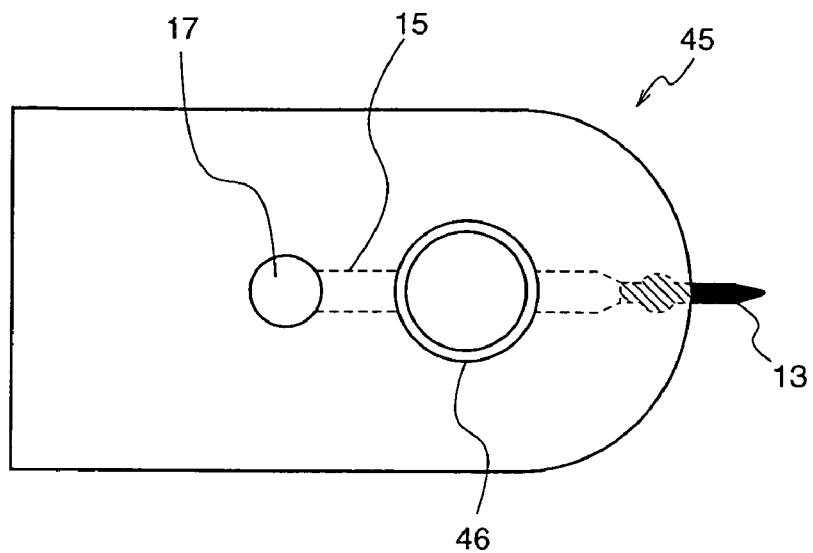
FIG. 8 is a plan view of a blood sensor according to a sixth embodiment of the present invention.

FIG. 8 is a plan view of a blood sensor 45 according to a sixth embodiment of the present invention. In FIG. 8, the same reference numerals as those shown in FIGS. 1 to 7 denote the same components, and therefore, repeated description is not necessary.

The blood sensor 45 is a kind of an optical sensor, and the degree of color change in a detection part 46 is converted into a blood glucose level by measuring an absorbance.

For this purpose, at least one of an upper surface and a lower surface of the detection part 46 is formed of a transparent material, and detection light is applied to the detection part 46 through the transparent material, and the degree of light change is read from the reflected light.

As described above, since the blood sensor according to the sixth embodiment reads the degree of light change from the reflected light, the contact electrodes 18a to 21a described for the first embodiment can be dispensed with.

Accordingly, the size of the blood sensor 45 can be reduced by just that much.

Embodiment 7

Figure 9:
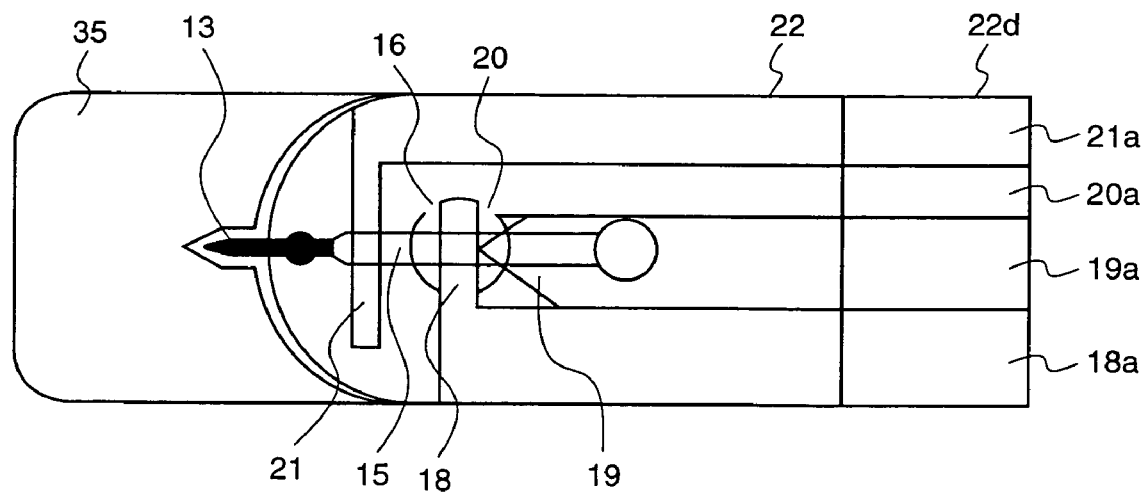
FIG. 9 is a transparent plan view of a blood sensor inserted into a blood testing apparatus according to a seventh embodiment of the present invention.

FIG. 9 is a perspective plan view of a blood sensor 11 according to a seventh embodiment of the present invention. In FIG. 9, the same components as those described with respect to the first embodiment are given the same reference numerals to simplify the description.

On the substrate 22, the detection electrodes 18, 19, 20, and 21 are disposed, and these detection electrodes 18~21 function as, for example, a working electrode, a sensing electrode, a counter electrode, and a hematocrit electrode, respectively.

These detection electrodes 18, 19, 20, and 21 are connected to the contact electrodes 18a, 19a, 20a, and 21a that are disposed on the other end 22d of the substrate 22, respectively. While in the following description the detection electrode 21 is used for detecting a Hct (hematocrit) value, the detection electrode 21 may be used for measuring, not only a Hct value, but also an amount of interfering substance that adversely affects the analytical value.

Next, a description will be given of the construction of the blood testing apparatus 50 according to the seventh embodiment, with reference to FIGS. 10(a)-10(e) and 11.

Figure 10A:
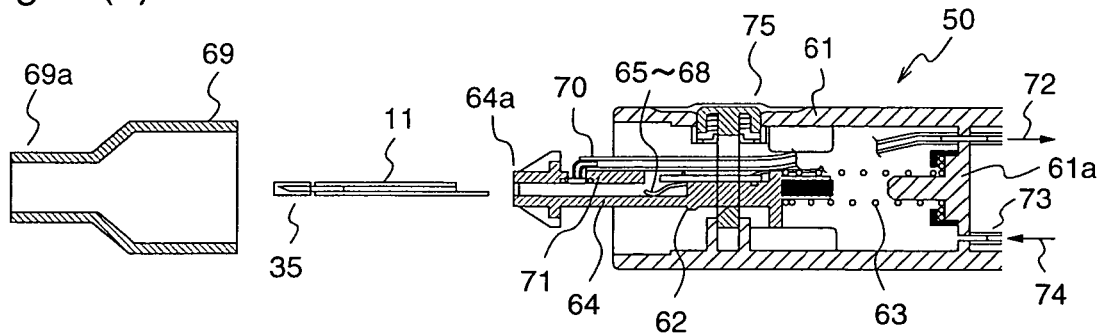
FIG. 10(a)-10(e) are cross-sectional views of a blood testing apparatus according to the seventh embodiment.
Figure 10B:
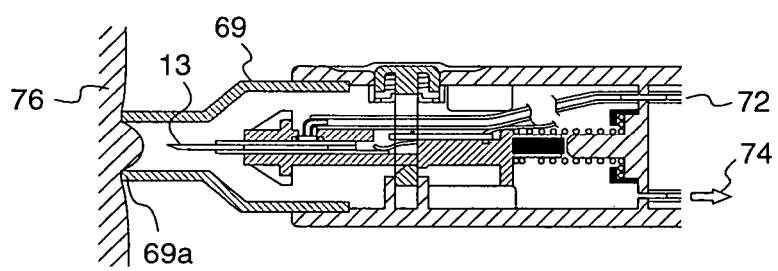
Figure 10C:
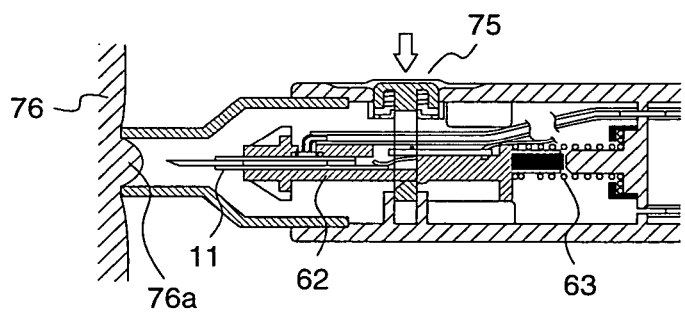
Figure 10D:
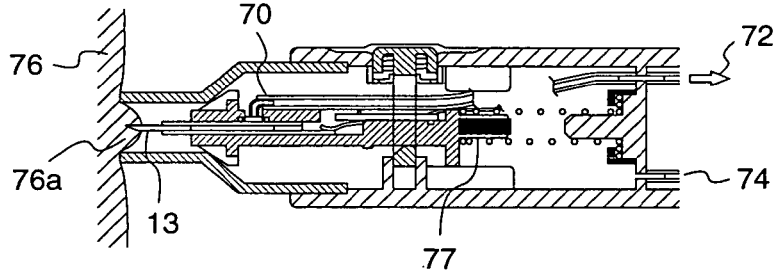
Figure 10E:
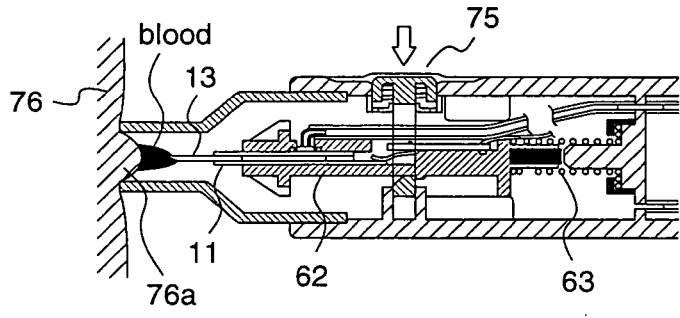
Figure 11:
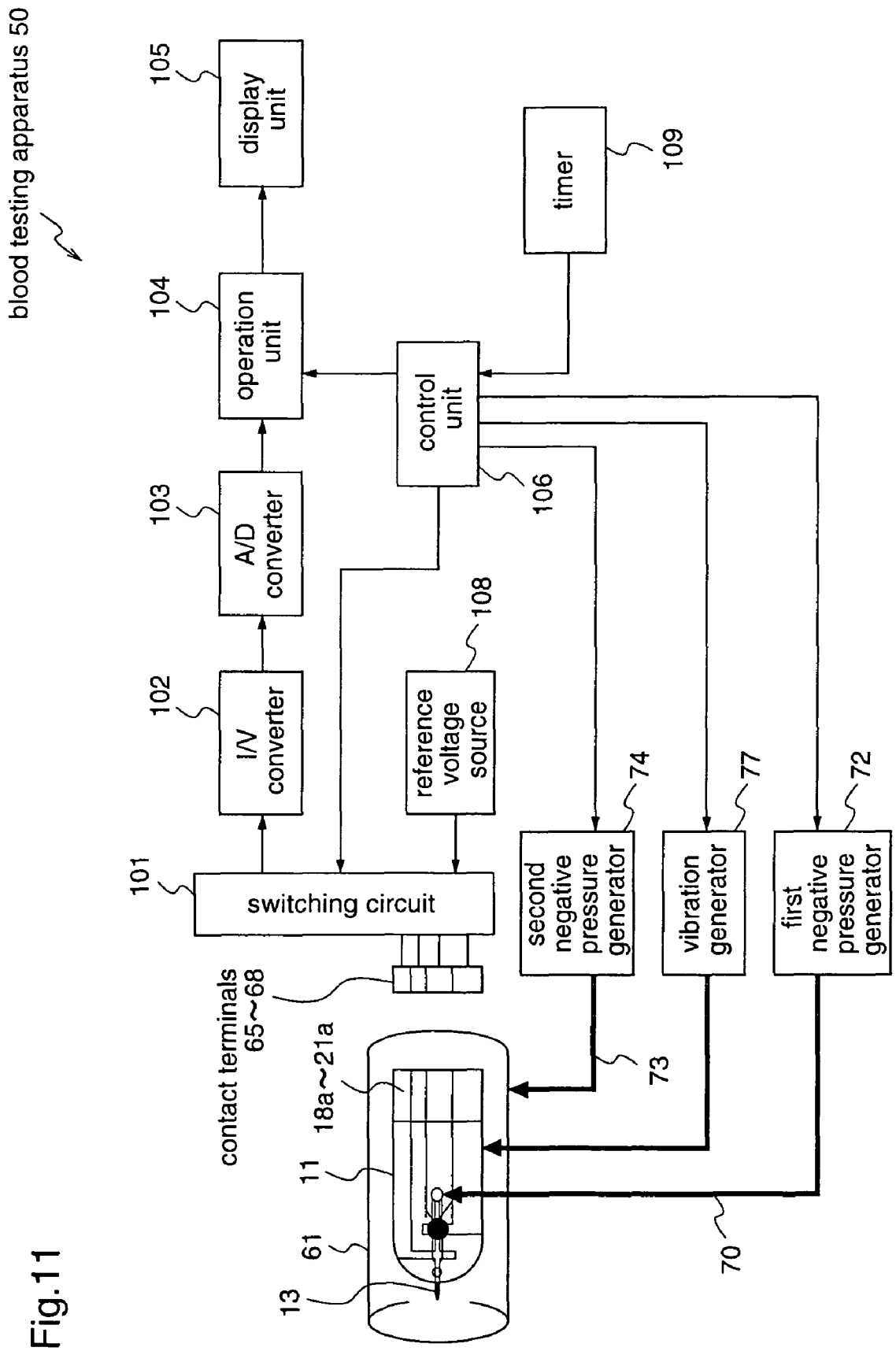
FIG. 11 is a block diagram of the blood testing apparatus according to the seventh embodiment.

FIGS. 10(a)-10(e) are cross-sectional views specifically illustrating the blood sensor 11 and the blood sensor insertion part of the blood testing apparatus 50 according to the seventh embodiment, and FIG. 11 is a block diagram illustrating the entire structure of the blood testing apparatus 50. In these figures, the same components are given the same reference numerals to simplify the description.

In FIG. 10(a), reference numeral 61 denotes a cylindrical casing, and the casing 61 includes a slider 62 that is disposed slidably in an anteroposterior direction (horizontal direction in the figure). Reference numeral 63 denotes a coil spring that is fixed to the casing 61, and the coil spring 63 pushes the slider 62 forward. Reference numeral 64a denotes a blood sensor insertion port, and this insertion port 64a is disposed at a front end of the slider 62. An insertion path 64 is connected to the insertion port 64a. Further, contact terminals 65, 66, 67, and 68 to be connected to the contact electrodes 18a, 19a, 20a, and 21a provided on the blood sensor 11 are disposed in the inner part of the insertion path 64.

Reference numeral 35 denotes a blood collection needle cover that covers the blood collection needle 13 of the blood sensor 11.

Reference numeral 69 denotes a cylindrical cap that covers the blood sensor 11, and its front and rear ends are opened. The cap 69 is put on the front end of the casing 61. Reference numeral 70 denotes a hollow tube having elasticity. An end of the tube 70 is connected to an upper portion of the insertion path 64 so that it is attached tightly to the inlet of the negative pressure generation part 17 provided on the upper surface of the blood sensor 11 when the blood sensor 11 is inserted.

Reference numeral 71 denotes an O ring formed of rubber having elasticity. This O ring 71 fixes an end of the tube 70 to the slider 62, and also improves the degree of attachment to the inlet of the negative pressure generation part 17. The other end of the tube 70 is connected to a first negative pressure generator 72. The first negative pressure generator 72 has a function of reducing the pressure in the hollow portion of the blood collection needle 13.

Reference numeral 73 denotes a tube an end of which is fixed to the casing 61, and the other end of this tube 73 is connected to a second negative pressure generator 74.

The second negative pressure generator 74 has a function of reducing the pressure in the casing 61 including the cap 69. Reference numeral 75 denotes a Lansing button (used as an example of a blood collection button) that makes the slider 62 protrude forward.

Further, reference numerals 65~68 denote contact terminals to be connected to the contact electrodes 18a~21a of the blood sensor 11, respectively.

As shown in FIG. 11, the contact terminals 65~68 are connected to a switching circuit 101, and an output of the switching circuit 101 is connected to an input of a current/voltage converter (I/V converter) 102.

An output of the I/V converter 102 is connected to an input of an operation unit 104 through an analog/digital converter (A/D converter) 103.

An output of the operation unit 104 is connected to a display unit 105 comprising liquid crystal.

Further, a reference voltage supply 108 is connected to the switching circuit 101. The reference voltage supply 108 may be a ground voltage.

Reference numeral 106 denotes a control unit, and an output of the control unit 106 is connected to a control terminal of the switching circuit 101, the operation unit 104, a timer 109, the first negative pressure generator 72, the second negative pressure generator 74, and a vibration generator 77.

An output of the vibration generator 77 is connected to the slider 62. The vibration generator 77 vibrates the slider 62, thereby to vibrate the blood collection needle 13 of the blood sensor 11.

Figure 12:
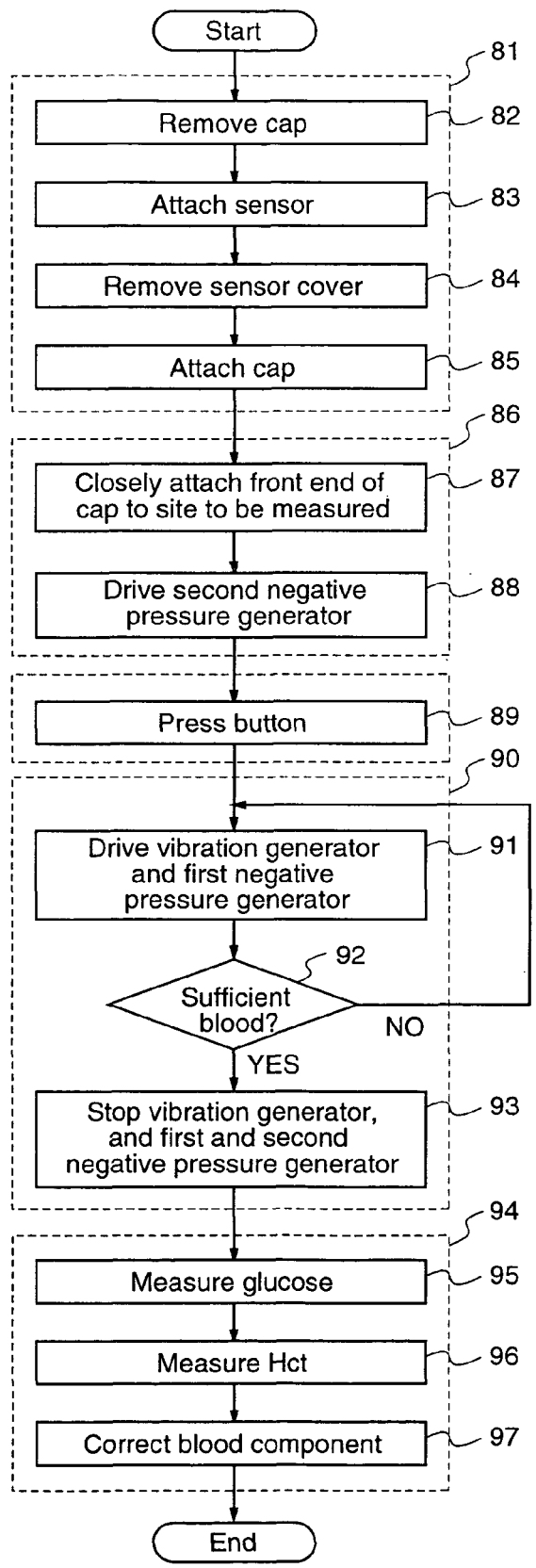
FIG. 12 is a flowchart for explaining a blood testing process according to the seventh embodiment.

Hereinafter, a description will be given of the operation of the blood testing apparatus 50 according to the seventh embodiment constituted as mentioned above, with reference to FIGS. 10~12. FIG. 12 is a flowchart illustrating a sequence of operations of the blood testing apparatus according to the seventh embodiment.

With reference to FIG. 12, initially, step 81 of attaching the blood sensor 11 to the blood testing apparatus 50 will be described.

The attachment step 81 corresponds to FIG. 10(*a*).

That is, the attachment step 81 includes step 82 of removing the cap 69 from the casing 61.

In step 83 that follows step 82, the blood sensor 11 is inserted in the insertion path 64 of the slider 62.

In this insertion step 83, the blood sensor 11 is inserted against the force applied by the coil spring 63, whereby the slider 62 is pressed into an inner part 61a of the casing 61.

That is, the slider 62 is set in a shoot position.

It is possible to detect whether the slider 62 is set at the shoot position or not, by checking whether the slider 62 is locked by the Lansing button 75 or not.

That is, when the slider 62 is locked, the hand of the user that pushes the slider 62 feels no resistance by the coil spring 63, whereby the user can sense that the slider 62 is set at the shoot position.

Further, it is possible to detect that the blood sensor 11 is attached to the slider 62, by detecting that the contact electrodes 18a~21a of the blood sensor 11 contact the contact terminals 65~68, respectively.

When the blood sensor 11 is attached to the slider 62, an end of the tube 70 is closely attached to the inlet of the negative pressure generation part 17.

Since the tube 70 connected to the first negative pressure generator 72 is closely attached to the inlet of the negative pressure generation part 17, it is possible to facilitate blood collection by reducing the pressure in the follow part of the blood collection needle 13.

As described above, in step 83, the blood sensor 11 is attached to the slider 62, and the slider 62 is set at the shoot position, and thereafter, the operation goes to step 84.

In step 84, the blood collection needle cover 35 of the blood sensor 11 is removed. Thereby, the blood collection needle 13 is exposed for the first time. Since the blood collection needle 13 has been covered with the blood collection needle cover 35 up to step 83, safety is ensured.

Next, the operation goes to step 85. In step 85, the cap 69 is attached to the casing 61.

In this state, the blood collection needle 13 is positioned behind the front end opening 69a of the cap 69.

The attachment step 81 of attaching the blood sensor 11 to the blood testing apparatus 50 is completed in step 85.

Since the cap 69 is put on the blood sensor 11 when the attachment step 81 is ended, the blood collection needle 13 is not exposed, whereby safety is secured and the patient is not scared by the needle 13.

Moreover, since the cap 69 is attached, even when the blood testing apparatus 50 is dropped to the floor or the like, there occurs no accident such as breakage of the blood collection needle 13.

Next, a description will be given of puncture preparation step 86. FIG. 10(*b*) corresponds to the puncture preparation step.

That is, in the puncture preparation step 86, initially, the front end opening 69a of the cap 69 is pressed against skin 76 of a measurement site so that the cap 69 closely contact the skin 76, in step 87. Next, in step 88, the pressure in the cap 69 is reduced by using the second negative pressure generator 74.

Thereby, the skin 76 is tensed and plumped up.

At this time, it is possible to perform the pressure reduction by using both the first negative pressure generator 72 and the second negative pressure generator 74. The pressure reduction is performed to reach a predetermined pressure level, thereby completing the puncture preparation step 86.

Next, a description will be given of puncture operation step 89. FIG. 10(*c*) corresponds to the puncture operation step 89.

That is, in the puncture operation step 89, the Lansing button 75 is pressed. Then, the lock mechanism is released, and the blood sensor 11 that is pushed back by the coil spring 63 is swiftly shot toward the plumped-up portion 76a of the skin 76, together with the slider 62.

At this time, since the plumped-up portion 76a of the skin 76 is tensed by the second negative pressure generator 74, even when a plastic needle 13 having elasticity is used, the needle 13 can easily run into the skin 76.

At this time, the front end of the blood collection needle 13 protrudes from the front end opening 69a of the cap 69.

Next, a description will be given of blood collection step 90. FIG. 10(*d*) corresponds to this blood collection step 90.

That is, in the blood collection step 90, initially, the skin 76 of the patient is punctured with the blood collection needle 13 in step 91, and in this state, the vibration generator 77 is driven and the first negative pressure generator 72 is also driven, whereby the pressure in the hollow part of the blood collection needle 13 is reduced from the negative pressure generation part 17 of the blood sensor 11 to perform aspiration of blood.

In this way, since the first negative pressure generator 72 is driven, the hollow part of the blood collection needle 13 is depressurized, whereby blood collection is facilitated. Further, since the vibration generator 77 is driven, blood collection is further facilitated.

Furthermore, in the blood testing apparatus 50, the switching circuit 101 is controlled according to an instruction of the control unit 106 so that the detection electrode 18 that serves as a working electrode to measure an amount of blood component is connected to the I/V converter 102 through the contact terminal 65, and the detection electrode 19 that serves as a sensing electrode to sense a flow of blood is connected to the reference voltage supply 108 through the contact terminal 66.

A constant voltage is applied between the detection electrode 10 and the detection electrode 19.

In this state, when the blood reaches the detection electrode 19 of the blood sensor 11, current flows between the detection electrodes 18 and 19. The current flowing between the detection electrodes 18 and 19 is converted into voltage by the I/V converter 102, and the voltage value is converted into a digital value by the A/D converter 103 to be outputted to the operation unit 104.

Then, the operation unit 104 detects that the blood flows into the blood sensor 11, on the basis of the digital value.

Also in the following step 92, collection of blood from the skin 76 is easily carried out due to aspiration by the negative pressure generating operation and vibration by the vibrating operation.

Further, the blood collected from the blood collection needle 13 is introduced to the detection part 16 through the supply path 15 due in part to capillary phenomenon.

When the blood introduced to the detection part 16 reaches the detection electrode 19 as a sensing electrode, the current that flows between the detection electrodes 18 and 19 is detected by the operation part 104 as described above, whereby it is judged that a sufficient amount of blood to be measured is introduced, followed by step 93.

Since blood collection is stopped when the collected blood reaches the detection electrode 19, collection of excess blood is prevented, i.e., a minimum necessary amount of blood is collected, whereby the burden on the patient is minimized.

In step 93, the operations of the first negative pressure generator 72, the second negative pressure generator 74, and the vibration generator 77 are stopped.

When the first negative pressure generator 72 is stopped, the blood that flows inward from the blood collection needle 13 is prevented from flowing from the negative pressure generation part 17 toward the tube 70.

That is, the collected blood is prevented from leaking out of the blood sensor 11.

When the second negative pressure generator 74 is stopped to open the inside of the cap 69 to atmosphere pressure, the plumped-up portion 76a of the skin 76 disappears, and the skin 76 turns back.

After the skin 76 turns back, the blood collection needle 13 is removed. On the other hand, if the collected blood does not reach the detection electrode 19 that senses flow of blood in step 92, it means shortage of analyte (blood), and further aspiration of blood is carried out in step 91.

At this time, if the blood does not reach the detection electrode 19 even when a predetermined period of time has passed, the blood testing apparatus 50 displays "error", and stops further aspiration of blood.

The blood collection step 90 may be altered such that blood collection is carried out after removing the needle 13 from the skin 76 as shown in FIG. 10(*e*), while in FIG. 10(*d*) it is carried out with the needle 13 being inserted in the skin 76.

That is, in step 90, after the skin 76 of the patient is punctured with the blood collection needle 13 in the puncture step 89, the needle 13 is immediately taken out of the skin 76.

Then, the first and second negative pressure generators 72 and 74, are operated, and the patient waits in this state until blood spills out of the punctured skin 76.

After a predetermined period of time has passed, blood spills out of the skin 76 as shown in FIG. 10(*e*), and then the blood collection needle 13 is moved to a position where the needle tip contacts the blood. Thereby, the blood collected by the needle 13 can be introduced to the detection part 16 through the supply path 15.

When the blood collection step 90 is completed, the operation goes to blood glucose level measurement step 94.

In the blood glucose level measurement step 94, initially, an amount of glucose is measured in step 95.

Measurement of an amount of glucose is carried out as follows. After glucose in blood and glucose oxidation-reduction enzyme are reacted for a predetermined period of time, voltage is applied between the detection electrode 18 as a working electrode and the detection electrode 20 as a counter electrode.

To be specific, in step 95, initially the switching circuit 101 is controlled according to an instruction of the control unit 106 so that the detection electrode 18 that serves as a working electrode for measuring an amount of glucose is connected to the I/V converter 102 through the contact terminal 65, and the detection electrode 20 that serves as a counter electrode for measuring an amount of glucose is connected to the reference voltage supply 108 through the contact terminal 67.

While the glucose in blood and the glucose oxidation-reduction enzyme are reacted for a predetermined period of time, the I/V converter 102 and the reference voltage supply 108 are turned off. After a predetermined period of time (1~10 sec) has passed, constant voltage (0.2~0.5V) is applied between the detection electrodes 10 and 20 for a predetermined period of time (1~5 sec) under instruction of the control unit 106. The reaction time and the voltage application time are measured by a timer 109.

Then, the mediator in the reduced state, which occurs on the detection electrode 18 by enzyme reaction, is oxidized, and the oxidation current is detected between the detection electrodes 18 and 20.

This current is converted into voltage by the I/V converter 102, and the voltage value is converted into a digital value by the A/D converter 103 to be outputted to the operation unit 104.

The operation unit 104 converts the digital value into an amount of glucose.

Next, measurement of Hct value is carried out in step 96.

Initially, the switching circuit 101 is controlled according to an instruction of the control unit 106 so that the detection electrode 21 that serves as a working electrode for measuring a Hct value is connected to the I/V converter 102 through the contact terminal 68, and the detection electrode 18 that serves as a counter electrode for measuring a Hct value is connected to the reference voltage supply 108.

Then, according to an instruction of the control unit 106, a constant voltage (2V~3V) is applied between the detection electrodes 21 and 18 from the I/V converter 102 and the reference voltage supply 108.

Thereby, current that depends on the Hct value is detected between the detection electrodes 21 and 18.

The current that flows between the detection electrodes 21 and 18 is converted into voltage by the I/V converter 102, and the voltage value is converted into a digital value by the A/D converter 103 to be outputted to the operation unit 104.

The operation unit 104 calculates a Hct value on the basis of the digital value.

This Hct value is used for correction during glucose measurement.

This correction may use a Hct value which is obtained from a previously formed analytical curve between current and Hct value. Alternatively, the detected current may be used as it is.

In step 96, the applied voltage is 2~3V, and the application time is 0.01~5 sec.

In step 96, no mediator is disposed on the detection electrode 21 as a working electrode, the detection electrodes 21 and 18 are separated at an interval, and only blood exists in this interval. Therefore, it is possible to detect oxidation current that depends on the Hct value, without being affected by the reagent 25.

Finally, the blood component is corrected in step 97. That is, the amount of glucose obtained in step 95 is corrected using the Hct value detected in step 96.

This correction is carried out on the basis of a previously formed analytical curve (including an analytical table).

The corrected amount of glucose is displayed on the display unit 105 of the blood testing apparatus 50.

The used blood sensor 11 after completion of the blood glucose level measurement step 94 is discarded every time a measurement is ended.

In the above-described blood testing apparatus 50 that measures blood glucose level using the blood sensor 11 according to the seventh embodiment, the blood sensor 11 is attached to the slider 26 included in the blood testing apparatus 50, and the cap 69 is attached to the casing 61, and then the target site is punctured with the blood collection needle 13 that is provided on the blood sensor 11. Thereafter, the hollow part of the needle 13 is depressurized by the negative pressure generation part 17 an end of which is connected to the first negative pressure generator 72 to facilitate collection of blood, the collected blood is guided to the detection part 16 through the supply path 15, the component of the blood guided to the detection part 16 is reacted with a reagent to generate current, and detection of blood glucose level is carried out on the basis of the generated current. Therefore, puncture and blood collection can be simultaneously carried out by using the blood collection needle 13, and further, the collected blood can be tested as it is in the blood testing apparatus 50 without intervening manual work.

Further, since the cap 69 is attached to the blood sensor 11 when blood collection is carried out by using the blood collection needle 13, the blood collection needle 13 is not exposed, whereby safety is secured and the patient is not scared by the needle 13. Further, even when the blood testing apparatus 50 is dropped to the floor or the like, there occurs no accident such as breakage of the blood collection needle 13.

Further, when performing the blood collection, the front end opening 69a of the cap 69 is pressed against the skin 76 of the target site, and then the inside of the cap 69 is depressurized by the second negative pressure generator 74 so that the skin 76 is tensed and plumped up, and thereafter, the plumped-up portion 76a of the skin 76 is punctured with the blood collection needle 13. Therefore, the puncture is facilitated.

Moreover, during the blood collection, since the first negative pressure generator 72 and the vibration generator 77 are driven, the blood collection is further facilitated.

When the blood that is guided to the detection part 16 through the supply path 15 reaches the detection electrode 19 as a sensing electrode, it is judged that a necessary amount of blood is supplied, and thereby the blood collection is completed. Therefore, a minimum necessary amount of blood can be collected without collecting an excess amount of blood, whereby the burden on the patient can be minimized.

Moreover, while in the above-description the blood collection is carried out with the needle 13 being inserted in the skin 76, blood collection may be carried out as follows. That is, the needle 13 is taken out of the skin 76 of the patient immediately after the skin 76 is punctured with the blood collection needle 13 in the puncture step 89, and the patient waits for a while until blood spills out of the punctured skin 76 with the first and second negative pressure generators being continuously driven, and the blood collection needle 13 is moved to a position where the needle tip contacts the blood when the blood spills out of the skin 76, thereby collecting the blood. Thus, the burden on the patient can be further reduced.

Embodiment 8

Figure 13:
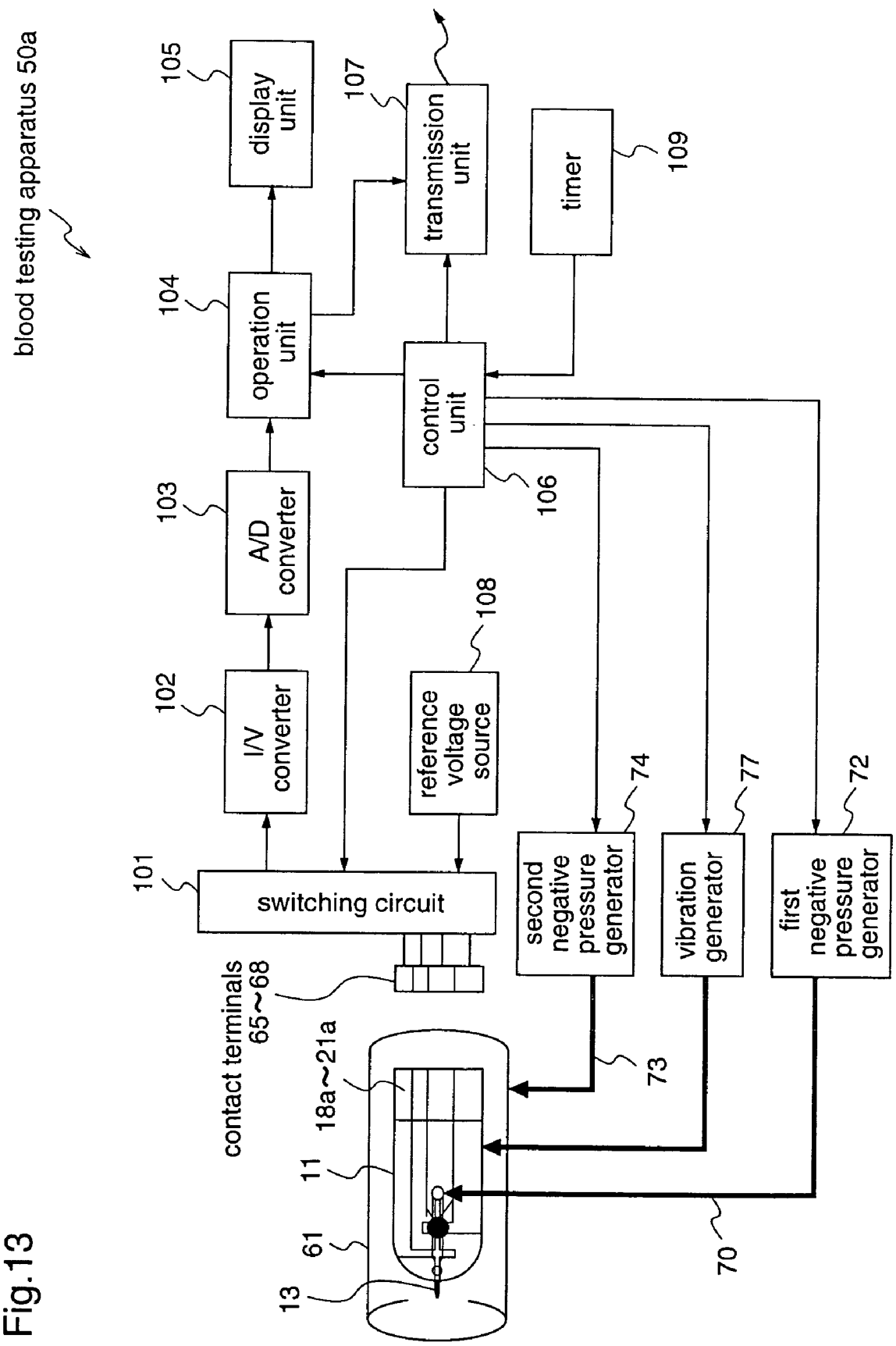
FIG. 13 is a block diagram of a blood testing apparatus according to an eighth embodiment.
Figure 14:
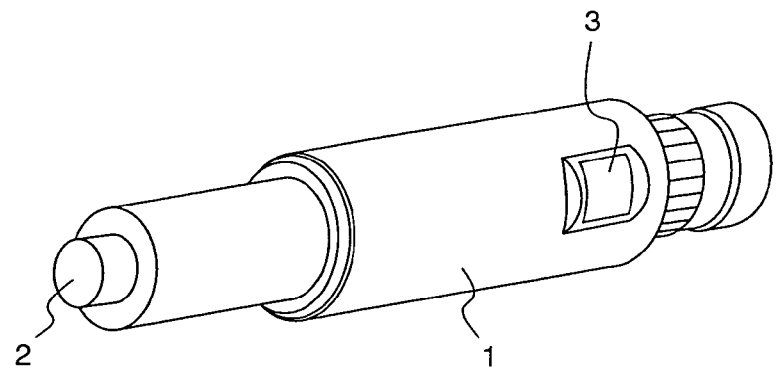
FIG. 14 is a perspective view of a conventional puncture apparatus.
Figure 15:
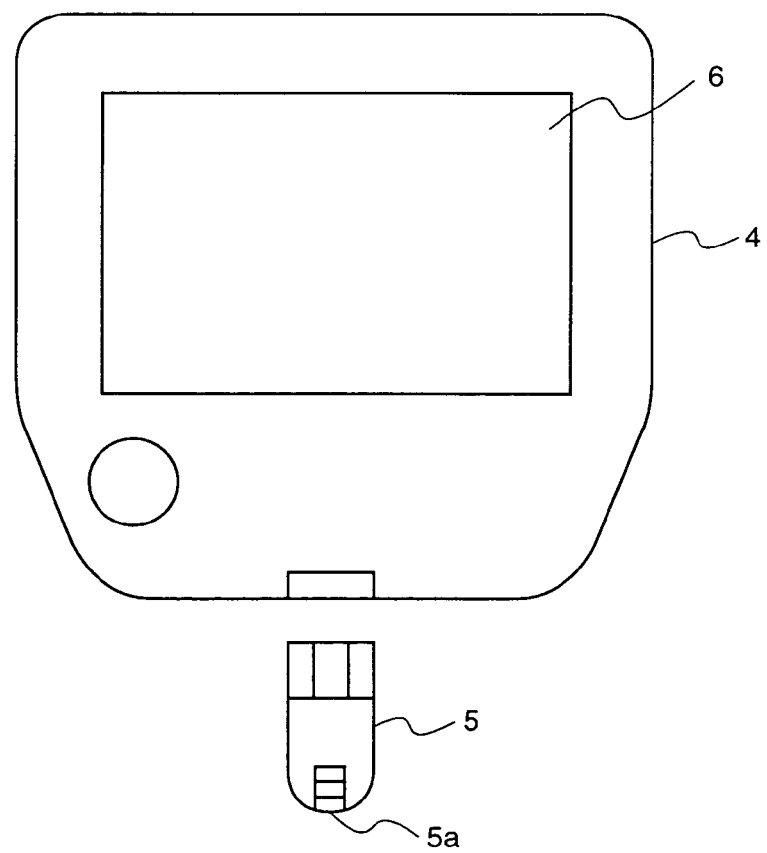
FIG. 15 is a plan view of a conventional measurement apparatus.

FIG. 13 is a block diagram illustrating a blood testing apparatus 50a according to an eighth embodiment of the present invention.

With reference to FIG. 13, reference numeral 107 denotes a transmission unit for transmitting a measured value obtained by the blood testing apparatus 50 to an external device. The transmission unit 107 is connected to the control unit 106 and the operation unit 104.

Next, a description will be given of the operation of the blood testing apparatus 50a using the blood sensor 11 according to the eighth embodiment.

Initially, the switching circuit 101 is controlled according to an instruction of the control unit 106 so that the detection electrode 18 that serves as a working electrode to measure an amount of blood component is connected to the I/V converter 102 through the contact terminal 65.

Further, the detection electrode 19 that serves as a sensing electrode to sense flow of blood is connected to the reference voltage supply 108 through the contact terminal 66.

Then, a constant voltage is applied between the detection electrodes 18 and 19.

In this state, when blood is introduced, current flows between the detection electrodes 18 and 19. The current is converted into voltage by the I/V converter 102, and the voltage value is converted into a digital value by the A/D converter 103 to be outputted to the operation unit 104. In the operation unit 104, it is detected that blood flows in on the basis of the digital value.

Next, measurement of glucose as a blood component is carried out.

Initially, the switching circuit 101 is controlled according to an instruction of the control unit 106 so that the detection electrode 18 that serves as a working electrode to measure an amount of glucose is connected to the I/V converter 102 through the contact terminal 65.

Further, the detection electrode 20 that serves as a counter electrode to measure an amount of glucose is connected to the reference voltage supply 108 through the contact terminal 67.

The I/V converter 102 and the reference voltage supply 108 are turned off during a predetermined period of time wherein the glucose in blood and an oxidation-reduction enzyme are reacted to each other. After a predetermined period of time (1~10 sec) has passed, a constant voltage (0.2~0.5V) is applied between the detection electrodes 18 and 20 under instruction of the control unit 106.

In this state, when reaction occurs, current flows between the detection electrodes 18 and 20, and this current is converted into voltage by the I/V converter 102, and further, the voltage value is converted into a digital value by the A/D converter 103 to be outputted to the operation unit 104. In the operation unit 104, the digital value is converted into an amount of glucose.

After the amount of glucose is measured, measurement of a Hct value is carried out.

Initially, the switching circuit 101 is controlled according to an instruction of the control unit 106 so that the detection electrode 21 that serves as a working electrode to measure a Hct value is connected to the I/V converter 102 through the contact terminal 68.

Further, the detection electrode 18 that serves as a counter electrode to measure a Hct value is connected to the reference voltage source 108.

Then, according to an instruction from the control unit 106, a constant voltage (2V~3V) is applied between the detection electrodes 21 and 18 from the I/V converter 102 and the reference voltage supply 108.

The current flowing between the detection electrodes 21 and 18 is converted into voltage by the I/V converter 102, and the voltage value is converted into a digital value by the A/D converter 103 to be outputted to the operation unit 104.

The operation unit 104 converts the digital value into a Hct value.

With reference to an analytical curve or an analytical curve table which has previously been obtained using the measured Hct value and the amount of glucose component, the amount of glucose component is corrected with the Hct value, and the result of correction is displayed on the display unit 105.

Further, the corrected result is transmitted from the transmission unit 107 toward an injection unit (not shown) for injecting insulin (an example of curative).

Although this transmission may use radio wave, optical communication that has no interference to medical equipment is preferable.

Since the measured data thus corrected is transmitted from the transmission unit 107, a dose of insulin is automatically set in the injection unit.

Accordingly, the patient is saved from the trouble of setting the dose of insulin to be administered, on the injection unit.

Further, since the dose of insulin is set on the injection unit without intervening artificial means, setting error can be avoided.

In the blood testing apparatus 50a using the blood sensor 11 according to the eighth embodiment of the present invention, since the data measured and corrected by the blood testing apparatus 50a is transmitted from the transmission unit 107 to an external device such as an insulin injection unit, the dose of insulin can be automatically set on the injection unit. Therefore, it is not necessary for the patient to set the dose of insulin on the injection unit, whereby the patient is saved from the trouble of setting the same. Further, since the dose of insulin is set on the injection unit without intervening artificial means, setting error can be avoided.

While in the embodiments of the present invention measurement of glucose has been described, the present invention is also applicable to measurement of blood components such as lactic acid and cholesterol.

APPLICABILITY IN INDUSTRY

Since a blood sensor according to the present invention can easily perform blood test, it is applicable to a blood testing apparatus and the like.

What is claimed is:
1. A blood sensor comprising:
a base;
a needle for blood collection which is disposed at a front end of the base, the blood collection needle having a tubular shape with a through-hole defining apertures at both ends thereof;
a detection part for detecting a component of blood collected by the blood collection needle, and a blood supply path for supplying the blood collected by the blood collection needle to the detection part, the detection part and the blood supply path being provided in the base;
a negative pressure supply path being connected to the blood supply path; and
a negative pressure generation part comprising a hole formed in the base for applying negative pressure to the hollow part of the blood collection needle through the negative pressure supply path, the negative pressure generation part being provided approximately at the center of the base,
the blood collection needle being provided in such a manner that it penetrates into the blood supply path;
the detection part being disposed between the blood collection needle and the negative pressure generation part; and
wherein the blood supply path shares a portion with the negative pressure supply path that forms the negative pressure generation part, and the detection part is provided at an end of the blood supply path that shares a portion with the negative pressure supply path.

2. A blood sensor as defined in claim 1 wherein detection electrodes are disposed on the detection part, and contact electrodes connected to the detection electrodes are disposed on an end surface of the base.

3. A blood sensor as defined in claim 1 wherein said needle is comprised of plastic.

4. A blood sensor as defined in claim 1 wherein said needle is hollow and has a circular cross section.

5. A blood sensor as defined in claim 1 wherein said needle is hollow and has a triangular cross section.

6. A blood sensor as defined in claim 1 wherein said needle is hollow and has a polygonal cross section.

7. A blood sensor as defined in claim 1, further comprising a blood collection needle cover that covers the blood collection needle and is formed integrally with the base such that the cover covers a front end portion of the base and includes a notch into which the needle is inserted with clearance.

8. A blood sensor as defined in claim 1 wherein a plurality of the blood collection needles are provided in parallel with each other at the front end of the base, and said blood supply path is in communication with each of the plural blood collection needles.

9. A blood sensor as defined in claim 1 wherein at least one surface of the detection part is comprised of a transparent material.

10. A blood testing apparatus comprising:
a cylindrical casing;
a slider that is forward or backward movably provided in the cylindrical casing;
a blood sensor as defined in claim 1, which is attached at a front end of the slider;
a first negative pressure generator for supplying negative pressure, via a conduit, to a negative pressure generation part provided in the blood sensor; and
a blood collection button for instructing the slider to move forward; and
said first negative pressure generator being connected to the negative pressure generation part via a tube.

11. A blood testing apparatus as defined in claim 10 wherein a cylindrical cap is provided at a front end of the casing.

12. A blood testing apparatus as defined in claim 11 further including a second negative pressure generator for supplying negative pressure, the second negative pressure generator being provided in the casing.

13. A blood testing apparatus as defined in claim 10 wherein forward movement of the slider is given momentum by a coil spring.

14. A blood testing apparatus as defined in claim 10 further including a vibration generator for vibrating the blood collection needle.

15. A blood testing apparatus comprising:
- a cylindrical casing;
- a slider provided in the cylindrical casing, wherein the slider is movable is a forward or backward direction of the cylindrical casing;
- a blood sensor as defined in claim 1, which is attached at a front end of the slider;
- a first negative pressure generator for supplying negative pressure, via a conduit, to a negative pressure generation part provided in the blood sensor;
- a blood collection button for enabling the slider to move forward;
- contact terminals to which the contact electrodes provided in the blood sensor are connected, said contact terminals being provided on the slider;
- a measurement unit for measuring a component of blood that is collected and detected by the blood sensor, said measurement unit being connected to the contact terminals; and
- a tube connecting the first negative pressure generator to the negative pressure generation part.

16. A blood testing apparatus as defined in claim 15 wherein said measurement unit comprises:
- an I/V converter connected to the contact terminals;
- an A/D converter to which an output of the I/V converter is connected;
- an operation unit having an input to which an output of the A/D converter is connected, and the other input to which an output of a control unit is connected; and
- a display unit to which an output of the operation unit is connected.

17. A blood testing apparatus as defined in claim 16 further including a transmission unit for transmitting the result of operation obtained by the operation unit, said transmission unit being connected to the control unit.

18. A method for controlling a blood testing apparatus as defined in claim 15, comprising:
- an attachment step of attaching the blood sensor to the blood testing apparatus;
- a puncture preparation step of applying the blood testing apparatus to a measurement site, after the attachment step;
- a puncture operation step of puncturing the measurement site with the blood collection needle, after the puncture preparation step;
- a blood collection step of applying negative pressure to the hollow part of the blood collection needle by the first negative pressure generator to collect blood from the measurement site, after the puncture operation step; and
- a measurement step of detecting and measuring a component of the collected blood, after the blood collection step.

19. A method for controlling a blood testing apparatus as defined in claim 18 wherein, in the blood collection step, the blood collection needle is vibrated by a vibration generator.

20. A method for controlling a blood testing apparatus as defined in claim 18 wherein, in the attachment step, a cap is put on the front end of the casing of the blood testing apparatus after a blood collection needle cover that covers the blood collection needle of the blood sensor is removed.

21. A method for controlling a blood testing apparatus as defined in claim 20 wherein, in the puncture preparation step, the cap is applied to a measurement site, and negative pressure is added into the casing of the blood testing apparatus including the cap by the second negative pressure generator.

22. A method for controlling a blood testing apparatus as defined in claim 18 wherein, after the measurement step, the measured data is transmitted to an injection unit for a curative drug.

* * * * *